United States Patent
Glassy et al.

(10) Patent No.: US 11,028,155 B2
(45) Date of Patent: Jun. 8, 2021

(54) ENHANCED DELIVERY OF DRUGS TO THE BRAIN

(71) Applicant: Nascent Biotech, Inc., San Diego, CA (US)

(72) Inventors: Mark C. Glassy, San Diego, CA (US); Rishab K. Gupta, Van Nuys, CA (US)

(73) Assignee: Nascent Biotech, Inc., San Diego, CA (US)

(*) Notice: Subject to any disclaimer, the term of this patent is extended or adjusted under 35 U.S.C. 154(b) by 0 days.

(21) Appl. No.: 15/261,725

(22) Filed: Sep. 9, 2016

(65) Prior Publication Data
US 2017/0073400 A1    Mar. 16, 2017

Related U.S. Application Data

(60) Provisional application No. 62/247,490, filed on Oct. 28, 2015, provisional application No. 62/217,608, filed on Sep. 11, 2015.

(51) Int. Cl.
| *C07K 16/18* | (2006.01) |
| *C07K 16/30* | (2006.01) |
| *A61K 47/68* | (2017.01) |
| *C07K 16/28* | (2006.01) |
| *A61K 39/00* | (2006.01) |

(52) U.S. Cl.
CPC .......... *C07K 16/18* (2013.01); *A61K 47/6865* (2017.08); *C07K 16/2887* (2013.01); *C07K 16/30* (2013.01); *A61K 2039/505* (2013.01); *C07K 2317/21* (2013.01)

(58) Field of Classification Search
CPC ............ A61K 47/6883; A61K 47/6803; A61K 39/395; C07K 16/18
See application file for complete search history.

(56) References Cited

U.S. PATENT DOCUMENTS

| 2002/0009444 A1 | 1/2002 | Grillo-Lopez et al. |
| 2002/0099179 A1 | 7/2002 | Jolliffe et al. |
| 2013/0287802 A1 | 10/2013 | Govindappa et al. |
| 2015/0218280 A1* | 8/2015 | Epstein et al. ..... C07K 16/2887 |

FOREIGN PATENT DOCUMENTS

| WO | 1989001343 | 2/1989 |
| WO | 2013055404 | 4/2013 |
| WO | 2014072741 | 5/2014 |
| WO | 2017044866 | 3/2017 |

OTHER PUBLICATIONS

Glassy et al., "Summary Analysis of the Pre-Clinical and Clinical Results of Brain Tumor Patients Treated With Pritumumab", Human Antibodies, vol. 18 Issue No. 4, 2009, pp. 127-137.
PCT/US2016/051128, "International Search Report and Written Opinion", dated Apr. 7, 2017, 15 pages.
PCT/US2016/051128, "Invitation to Pay Additional Fees and Partial Search Report", dated Dec. 12, 2016, 4 pages.
Anonymous, "Nascent Biotech's Pritumumab: The Future of Brain Cancer Immunotherapy", Available Online at, URL: https://born2invest.com/articles/nascent-biotechs-pritumumab-the-future-of-brain-cancer-immunotherapy, Mar. 31, 2015, 14 pages.
EP16845201.9, "Extended European Search Report", Apr. 9, 2019, 8 pages.
Vincke et al., "General Strategy to Humanize a Camelid Single-Domain Antibody and Identification of Universal Humanized Nanobody Scaffold", Journal of Biological Chemistry, vol. 284, No. 5, Nov. 14, 2008, pp. 3273-3284.

* cited by examiner

*Primary Examiner* — Robert C Hayes
(74) *Attorney, Agent, or Firm* — Kilpatrick Townsend & Stockton LLP

(57) ABSTRACT

Compositions and methods related to antibodies or antibody fragments which are capable of crossing the blood brain barrier are provided.

5 Claims, 5 Drawing Sheets

Specification includes a Sequence Listing.

ved in their
entirety.

ENHANCED DELIVERY OF DRUGS TO THE BRAIN

CROSS REFERENCE TO RELATED APPLICATIONS

This application claims priority to U.S. Provisional Application No. 62/217,608, filed Sep. 11, 2015 and U.S. Provisional Application No. 62/247,490, filed Oct. 28, 2015, both of which are incorporated herein by reference in their entirety.

BACKGROUND

The blood brain barrier (BBB) poses a significant barrier for the delivery of therapeutics to the brain. The BBB is a protective endothelial tissue surrounding the CNS and poses a major obstacle to the systemic delivery of therapeutic and diagnostic agents for the treatment of neurological diseases. For example, treatment of brain cancer or metastases of other solid tumors to the brain is a highly unmet need. The lack of good treatments is due to the invasive and infiltrating character of tumors in the brain, and the inability of most effective biologic agents to cross the BBB. If the BBB were leaky or can readily be overcome, then new and useful drugs could be delivered to brain tissues. Previous products designed to overcome or bypass the BBB have been difficult to control thereby limiting their usefulness.

The present disclosure satisfies these and other needs by providing antibodies or antibody fragments that are able to cross the BBB.

SUMMARY

Described herein are compositions and methods related to antibodies or antibody fragments which are able to cross the blood brain barrier.

In a first aspect, disclosed herein is a recombinant antigen binding protein comprising: (a) a heavy chain acceptor framework of SEQ ID NO: 1 and at least one heterologous variable heavy chain CDR specific for a desired antigen; and (b) a light chain acceptor framework of SEQ ID NO: 2 and at least one heterologous variable light chain CDR specific for a desired antigen.

In some embodiments, the recombinant antigen binding protein comprises three heterologous variable heavy chain CDRs and three heterologous variable light chain CDRs specific for a desired antigen. In some embodiments, the antigen is selected from an antigen listed in Table 1. In some embodiments, the variable heavy chain CDR sequence is specific for an antigen listed in Table 1. In some embodiments, the variable light chain CDR sequence is specific for an antigen listed in Table 1.

In some embodiments, the recombinant antigen binding protein has an isoelectric point of 8.0-9.0. In some embodiments, the recombinant antigen binding protein has an isoelectric point of about 8.7.

In some embodiments, the recombinant antigen binding protein is capable of crossing the blood brain barrier.

In some embodiments, the heavy chain acceptor framework is at least 90% identical to SEQ ID NO: 1. In some embodiments, the light chain acceptor framework is at least 90% identical to SEQ ID NO: 2.

In some embodiments, the antigen binding protein is a whole immunoglobulin, scFv, Fab fragment, F(ab')2, Fab fragments linked by a disulfide bridge at the hinge region, Fab' fragment, Fv, single domain antibody (Dab), nanobody, or bispecific antibody.

In another aspect, disclosed herein is a nucleic acid encoding the recombinant antigen binding protein of any of the aspects and embodiments above.

In another aspect, disclosed herein is an expression vector comprising the nucleic acid of any of the aspects and embodiments above. In another aspect, disclosed herein is a host cell comprising the expression vector of any of the aspects and embodiments above. In some embodiments, the host cell is a bacterial cell or eukaryotic cell, which can be a mammalian cell.

In another aspect, disclosed herein is a method of delivering a recombinant antigen binding protein across the blood brain barrier comprising administering a recombinant antigen binding protein in a therapeutically effective amount, wherein said recombinant antigen binding protein comprises (a) a heavy chain acceptor framework of SEQ ID NO: 1 and at least one heterologous variable heavy chain CDR specific for a desired antigen; and (b) a light chain acceptor framework of SEQ ID NO: 2 and at least one heterologous variable light chain CDR specific for a desired antigen.

In some embodiments, the recombinant antigen binding protein comprises three heterologous variable heavy chain CDRs and three heterologous variable light chain CDRs specific for a desired antigen. In some embodiments, the antigen is selected from an antigen listed in Table 1. In some embodiments, the variable heavy chain CDR sequence is specific for an antigen listed in Table 1. In some embodiments, the variable light chain CDR sequence is specific for an antigen listed in Table 1.

In some embodiments, the recombinant antigen binding protein has an isoelectric point of 8.0-9.0. In some embodiments, the recombinant antigen binding protein has an isoelectric point of about 8.7.

In some embodiments, the heavy chain acceptor framework is at least 90% identical to SEQ ID NO: 1. In some embodiments, the light chain acceptor framework is at least 90% identical to SEQ ID NO: 2.

In some embodiments, the antigen binding protein is a whole immunoglobulin, scFv, Fab fragment, F(ab')2, Fab fragments linked by a disulfide bridge at the hinge region, Fab' fragment, Fv, single domain antibody (Dab), nanobody, or bispecific antibody.

In a further aspect, disclosed herein is the use of the recombinant antigen binding proteins of the above aspects and embodiments for use in the treatment of cancer, infectious disease, autoimmune disorders, or transplantation rejection.

Provided are methods of delivering an agent to the brain of a subject, the method comprising administering to the subject a composition comprising a conjugate comprising pritumumab and one or more agents. Also provided are compositions and kits comprises a composition comprising a conjugate comprising pritumumab and one or more agents.

BRIEF DESCRIPTION OF THE DRAWINGS

FIG. 1 is a schematic diagram illustrating the use of CDR grafting to engineer new antigen binding specificities into the pritumumab framework to generate new antigen binding proteins that can cross the blood brain barrier. The CDRs of native pritumumab allow binding to ectodomain vimentin (EDV). The native pritumumab CDRs can be replaced with heterologous CDRs to generate binding specificities to antigens, Ag1, Ag2, Ag3, and the like.

DETAILED DESCRIPTION

Figure 1:
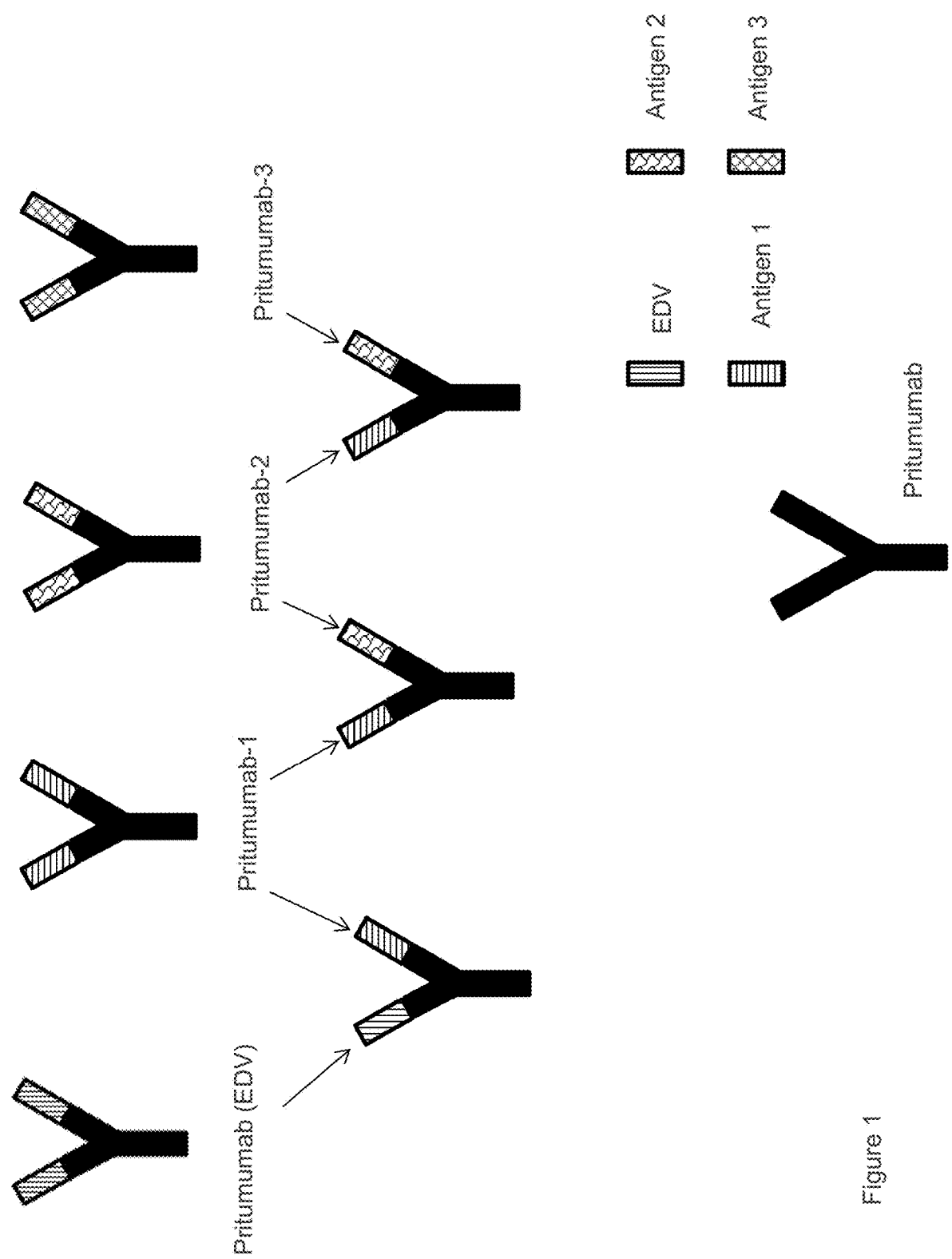

Monoclonal antibodies (mAbs) are antibodies of a single antigen specificity produced by identical immune cells, i.e., clones of a common germ cell. They offer unprecedented opportunities for drug development because of their ability to target almost any cell surface or secreted molecule with remarkable specificity, efficacy, and safety.

As is well known, complementarity determining region (CDR) segments are responsible for the ability of antibodies to bind to their target antigens. Differences between the variable domains are located on three loops known as hypervariable regions (HV-1, HV-2 and HV-3) or (CDR1, CDR2 and CDR3). CDRs are supported within the variable domains by conserved framework regions. The present disclosure relates to the use of the framework of a human natural monoclonal antibody (PRITUMUMAB) to graft hypervariable regions from other antibodies, such as, murine, chimerized, humanized, or human monoclonal antibodies (mAbs) to generate new antigen binding proteins that are able to cross the blood brain barrier.

The CDRs will be exchanged (as a group or individually) between Abs of differing specificity and affinity. Swapping CDRs (also called CDR grafting) is a technique that has been utilized for the humanization of murine antibodies, and also for the construction of more stable conventional antibody fragments. As discussed herein, the framework of pritumumab is of human origin and provides a unique characteristic of being able to cross the BBB, and since the CDRs are both highly variable and selected for binding affinity rather than stability it is proposed that variation in CDRs on the framework of human IgG1 (pritumumab) is an innovative approach to enhance clinical utility of monoclonal antibodies that are highly target specific to treat various human disorders but are not used due to their inability to cross the BBB. As disclosed herein, we will construct a series of CDR-swap mutants with the goal of understanding the contribution of the pritumumab framework to deliver target specific monoclonal antibodies containing CDRs of medical and therapeutic importance across the BBB.

Specifically, the present inventors have shown that pritumumab is a human antibody that readily crosses the BBB. By placing different specificities and/or payloads on the antibody then these specificities and/or payloads should be readily delivered to the brain. The pritumumab heavy chain serves as a carrier to cross the BBB and delivers the new specificity and/or payload. Thus, the present disclosure exploits a natural human antibody that readily crosses the BBB and uses this unique feature to deliver additional drugs.

Definitions

It is to be understood that this invention is not limited to particular methods, reagents, compounds, compositions or biological systems, which can, of course, vary. It is also to be understood that the terminology used herein is for the purpose of describing particular aspects only, and is not intended to be limiting. As used in this specification and the appended claims, the singular forms “a”, “an” and “the” include plural references unless the content clearly dictates otherwise.

The term “about” as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

“Vertebrate,” “mammal,” “subject,” “mammalian subject,” or “patient” are used interchangeably and refer to mammals such as human patients and non-human primates, as well as experimental animals such as rabbits, rats, and mice, cows, horses, goats, and other animals. Animals include all vertebrates, e.g., mammals and non-mammals, such as mice, sheep, dogs, cows, avian species, ducks, geese, pigs, chickens, amphibians, and reptiles.

“Treating” or “treatment” refers generally to either (i) the prevention of disease, e.g., prophylaxis, or (ii) the reduction or elimination of symptoms of a disease of interest, e.g., therapy. Thus, treatment can be prophylactic (to prevent or delay the onset of the disease, or to prevent the manifestation of clinical or subclinical symptoms thereof) or therapeutic suppression or alleviation of symptoms after the manifestation of the disease.

“Preventing” or “prevention” refers to prophylactic administration with compositions of the invention.

“Therapeutically-effective amount” or “an effective amount” refers to an amount of an antibody composition that is sufficient to prevent a disease or to alleviate (e.g., mitigate, decrease, reduce) at least one of the symptoms associated with a disease. It is not necessary that the administration of the composition totally eliminate the symptoms of the disease, as long as the benefits of administration of the composition outweigh the detriments. Likewise, the terms “treat” and “treating” in reference to a disease, as used herein, are not intended to mean that the subject is necessarily cured of the disease or that all clinical signs thereof are eliminated, only that some alleviation or improvement in the condition of the subject is effected by administration of the composition.

Antibodies and Fragments

As used herein, the term “antibody” refers to any immunoglobulin or intact molecule as well as to fragments thereof that bind to a specific epitope. Such antibodies include, but are not limited to polyclonal, monoclonal, chimeric, humanized, single chain, Fab, Fab', F(ab)' fragments and/or F(v) portions of the whole antibody and variants thereof. All isotypes are encompassed by this term, including IgA, IgD, IgE, IgG, and IgM.

As used herein, the term “antibody fragment” refers specifically to an incomplete or isolated portion of the full sequence of the antibody which retains the antigen binding function of the parent antibody. Examples of antibody fragments include Fab, Fab', F(ab')2, and Fv fragments; diabodies; linear antibodies; single-chain antibody molecules; and multispecific antibodies formed from antibody fragments.

An intact "antibody" comprises at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. The term antibody includes antigen-binding portions of an intact antibody that retain capacity to bind. Examples of binding include (i) a Fab fragment, a monovalent fragment consisting of the $V_L$, $V_H$, $C_L$ and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment (Ward et al., Nature, 341:544-546 (1989)), which consists of a VH domain; and (vi) an isolated complementarity determining region (CDR).

The term "antigen binding protein" refers to a molecule that contains all or a part of the antigen binding site of an antibody, e.g. all or part of the heavy and/or light chain variable domain, such that the antigen binding protein specifically recognizes a target antigen. Non-limiting examples of antigen binding proteins include full-length immunoglobulin molecules and scFvs, as well as antibody fragments, including but not limited to (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially a Fab with part of the hinge region (see, Fundamental Immunology (Paul ed., 3.sup.rd ed. 1993); (iv) a Fd fragment consisting of the $V_H$ and $C_{H1}$ domains; (v) a Fv fragment consisting of the $V_L$ and $V_H$ domains of a single arm of an antibody, (vi) a single domain antibody such as a Dab fragment (Ward et al., (1989) Nature 341:544-546), which consists of a $V_H$ or $V_L$ domain, a Camelid (see Hamers-Casterman, et al., Nature 363:446-448 (1993), and Dumoulin, et al., Protein Science 11:500-515 (2002)) or a Shark antibody (e.g., shark Ig-NARs Nanobodies™; and (vii) a nanobody, a heavy chain variable region containing a single variable domain and two constant domains.

The term "CDR" refers to one of the six hypervariable regions within the variable domains of an antibody that mainly contribute to antigen binding. One of the most commonly used definitions for the six CDRs was provided by Kabat E. A. et al., (1991) Sequences of proteins of immunological interest. NIH Publication 91-3242).

The term "antibody framework" as used herein refers to the part of the variable domain, either VL or VH, which serves as a scaffold for the antigen binding loops (CDRs) of this variable domain. In essence it is the variable domain without the CDRs.

As used herein, the term "single chain antibodies" or "single chain Fv (scFv)" refers to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., Science, 242:423-426 (1988); and Huston et al., Proc Natl Acad Sci USA, 85:5879-5883 (1988)). Such single chain antibodies are included by reference to the term "antibody" fragments and can be prepared by recombinant techniques or enzymatic or chemical cleavage of intact antibodies.

As used herein, the term "human sequence antibody" includes antibodies having variable and constant regions (if present) derived from human germline immunoglobulin sequences. The human sequence antibodies of the invention can include amino acid residues not encoded by human germline immunoglobulin sequences (e.g., mutations introduced by random or site-specific mutagenesis in vitro or by somatic mutation in vivo). Such antibodies can be generated in non-human transgenic animals, e.g., as described in PCT App. Pub. Nos. WO 01/14424 and WO 00/37504. However, the term "human sequence antibody", as used herein, is not intended to include antibodies in which CDR sequences derived from the germline of another mammalian species, such as a mouse, have been grafted onto human framework sequences (e.g., humanized antibodies).

Also, recombinant immunoglobulins can be produced. See, Cabilly, U.S. Pat. No. 4,816,567, incorporated herein by reference in its entirety and for all purposes; and Queen et al., Proc Natl Acad Sci USA, 86:10029-10033 (1989).

As used herein, the term "monoclonal antibody" refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences. In one aspect, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, the term "antigen" refers to a substance that prompts the generation of antibodies and can cause an immune response. It can be used interchangeably in the present disclosure with the term "immunogen". In the strict sense, immunogens are those substances that elicit a response from the immune system, whereas antigens are defined as substances that bind to specific antibodies. An antigen or fragment thereof can be a molecule (i.e., an epitope) that makes contact with a particular antibody. When a protein or a fragment of a protein is used to immunize a host animal, numerous regions of the protein can induce the production of antibodies (i.e., elicit the immune response), which bind specifically to the antigen (given regions or three-dimensional structures on the protein).

As used herein, the term "humanized antibody," refers to at least one antibody molecule in which the amino acid sequence in the non-antigen binding regions and/or the antigen-binding regions has been altered so that the antibody more closely resembles a human antibody, and still retains its original binding ability.

In addition, techniques developed for the production of "chimeric antibodies" (Morrison, et al., Proc Natl Acad Sci, 81:6851-6855 (1984), incorporated herein by reference in their entirety) by splicing the genes from a mouse antibody molecule of appropriate antigen specificity together with genes from a human antibody molecule of appropriate biological activity can be used. For example, the genes from a mouse antibody molecule can be spliced together with genes from a human antibody molecule of appropriate biological activity. A chimeric antibody is a molecule in which different portions are derived from different animal species, such as those having a variable region derived from a murine mAb and a human immunoglobulin constant region.

In addition, techniques have been developed for the production of humanized antibodies (see, e.g., U.S. Pat. Nos. 5,585,089 and 5,225,539, which are incorporated herein by reference in their entirety). An immunoglobulin light or heavy chain variable region consists of a "framework" region interrupted by three hypervariable regions, referred to as complementarity determining regions (CDRs). Briefly, humanized antibodies are antibody molecules from non-human species having one or more CDRs from the non-human species and a framework region from a human immunoglobulin molecule.

Alternatively, techniques described for the production of single chain antibodies can be adapted to produce single chain antibodies against an immunogenic conjugate of the present disclosure. Single chain antibodies are formed by linking the heavy and light chain fragments of the Fv region via an amino acid bridge, resulting in a single chain polypeptide. Fab and F(ab')2 portions of antibody molecules can be prepared by the proteolytic reaction of papain and pepsin, respectively, on substantially intact antibody molecules by methods that are well-known. See e.g., U.S. Pat. No. 4,342,566. Fab' antibody molecule portions are also well-known and are produced from F(ab')2 portions followed by reduction of the disulfide bonds linking the two heavy chain portions as with mercaptoethanol, and followed by alkylation of the resulting protein mercaptan with a reagent such as iodoacetamide.

The amino acid positions can be indicated according to the AHo numbering scheme. The AHo numbering system is described further in Honegger, A. and Pluckthun, A. (2001) J. Mol. Biol. 309:657-670). Alternatively, the Kabat numbering system as described further in Kabat et al. (Kabat, E. A., et al. (1991) Sequences of Proteins of Immunological Interest, Fifth Edition, U.S. Department of Health and Human Services, NIH Publication No. 91-3242) may be used. Conversion tables for the two different numbering systems used to identify amino acid residue positions in antibody heavy and light chain variable regions are provided in A. Honegger, J. Mol. Biol. 309 (2001) 657-670.

In one aspect, the present disclosure provides a human acceptor framework sequence for the grafting of CDRs from a heterologous source. The human pritumumab framework was found to be an especially useful framework.

Accordingly, the present invention provides an antigen binding protein acceptor framework comprising i) a variable heavy chain framework having at least 70% identity, preferably at least 75%, 80%, 85%, 90%, more preferably at least 95% identity, to SEQ ID No. 1; and/or (ii) a variable light chain framework having at least 70% identity, preferably at least 75%, 80%, 85%, 90%, more preferably at least 95% identity, to SEQ ID No. 2. These sequences are shown below:

SEQ ID NO. 1:
EVQLLESGGDLVQPGGSLRLSCAASGFTFSNYAMSWVRQAPGKGLEWVSA

ITPSGGSTNYADSVKGRFTISRDNSQNTLYLQMNSLRVEDTAVYICGRVP

YRSTWYPLYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK

SEQ ID NO: 2:
DIQMTQSPSSLSASVGDRVTITCRASQDISNYLAWFQQKPGKAPKSLIYA

ASSLHSKVPTQFSGSGSGTDFTLTISSLQPEDFATYYCLQYSTYPITFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

A general method for grafting CDRs into human acceptor frameworks has been disclosed by Winter in U.S. Pat. No. 5,225,539 and by Queen et al. in WO9007861A1, which are hereby incorporated by reference in their entirety.

In exemplary embodiments of the methods of the invention, the amino acid sequence of the CDR donor antibody is first identified and the sequences aligned using conventional sequence alignment tools (e.g., Needleman-Wunsch algorithm and Blossum matrices). The introduction of gaps and nomenclature of residue positions may be done using a conventional antibody numbering system. For example, the AHo numbering system for immunoglobulin variable domains may be used. The Kabat numbering scheme may also be applied since it is the most widely adopted standard for numbering the residues in an antibody. Kabat numbering may, e.g., be assigned using the SUBIM program. This program analyses variable regions of an antibody sequence and numbers the sequence according to the system established by Kabat and co-workers (Deret et al. 1995). The definition of framework and CDR regions is generally done following the Kabat definition which is based on sequence variability and is the most commonly used. Conversion tables for the two different numbering systems used to identify amino acid residue positions in antibody heavy and light chain variable regions are provided in A. Honegger, J. Mol. Biol. 309 (2001) 657-670. The Kabat numbering system is described further in Kabat et al. (Kabat, E. A., et al. (1991) Sequences of Proteins of Immunological Interest, Fifth Edition, U.S. Department of Health and Human Services, NIH Publication No. 91-3242). The AHo numbering system is described further in Honegger, A. and Pluckthun, A. (2001) J. Mol. Biol. 309:657-670).

For example, the acceptor frameworks disclosed herein can be used to generate a human or humanized antibody which retains the binding properties of the antibody from which the CDRs are derived. Accordingly, in a preferred embodiment the invention encompasses an antigen binding protein acceptor framework as disclosed herein, further comprising heavy chain CDR1, CDR2, and CDR3 and/or light chain CDR1, CDR2, and CDR3 from a donor antigen binding protein. Thus, in one embodiment, the invention provides an antigen binding protein specific to a desired antigen comprising (i) variable heavy and light chain CDRs; (ii) a human variable heavy chain framework having at least 70%, preferably at least 75%, 80%, 85%, 90%, 95%, or 100% identity to SEQ ID NO. 1; (iii) a human variable light chain framework having at least 70%, preferably at least 75%, 80%, 85%, 90%, 95%, or 100% identity to SEQ ID NO. 2.

Examples of antibodies with CDRs useful in the practice of the present disclosure include:

TABLE 1

| mAb | Manufacturer | Target/Antigen | First Indication |
|---|---|---|---|
| Rituximab | Roche/ | CD20 | B-cell lymphoma |
| Ibritumomab | BiogenIDEC | | |
| Tositumomab | Celldex GSK | | |
| Ofatumumab | GSK/Genmab | CD3 | CLL |
| Catumaxomab | Trion | CD3 and EPCAM | Ovarian cancer ascites |
| Gemtuzumab | Pfizer | CD33 | Acute myeloid Leukemi |
| Alemtuzumab | Genzyme | CD52 | B-cell leukemia |
| Eculizumab | Alexion | Complement Ca5 | Paroxysmal nocturnal hemoglobinuria |
| Cetuximab | Eli Lilly | EGFR | Colorectal cancer |
| Panitumumab | Amgen | | |

TABLE 1-continued

| mAb | Manufacturer | Target/Antigen | First Indication |
|---|---|---|---|
| Trastuzumab | Roche | HER2 | Breast cancer |
| Certoluzimab | UCB | VEGF | Crohn's disease |
| Bevacizumab | Roche | | Colorectal cancer |
| Ranibizumab | Roche | | Macular degeneration |
| Ipilimumab | | CD152 CTLA-4 | Melanoma |

Shown below is an alignment of the variable domains from a number of monoclonal antibodies approved for cancer treatment, as taken from Magdelaine-Beuzelin C, Kaas Q, Wehbi V, Ohresser M, Jefferis R, Lefranc M-P, Watier H. Structure-function relationships of the variable domains of monoclonal antibodies approved for cancer treatment. Critical Reviews in Oncology/Hematology. 64:210-225, 2007. Cetuximab (SEQ ID NO:3) VH domain at amino acids 1-119 and V-kappa domain at amino acids 120 to 226, Rituximab (SEQ ID NO:4) VH domain at amino acids 1 to 121 and V-kappa domain at amino acids 122-226, Alemtuzmab (SEQ ID NO:5) VH domain at amino acids 1 to 121 and V-kappa domain at amino acids 122-228, Bevacizumab (SEQ ID NO:6) VH domain at amino acids 1 to 123 and V-kappa domain at amino acids 124-230, Trastuzumab (SEQ ID NO:7) VH domain at amino acids 1 to 119 and V-kappa domain at amino acids 120-225, Pertuzumab (SEQ ID NO:8) VH domain at amino acids 1 to 119 and V-kappa domain at amino acids 120-226, Panitumumab (SEQ ID NO:9) VH domain at amino acids 1 to 96 and V-kappa domain at amino acids 97-184.

| VH domain | FR1-IMGT | CDR1-IMGT | FR2-IMGT | CDR2-IMGT |
|---|---|---|---|---|
| certuximab SEQ ID NO: 3 (1-119) | QVQLKQSGP.GLVQPSQSLSITCTVS | GFSL...TNYG | VHWVRQSPGKGLEWLGV | IWS...GNT |
| rituximab¹ SEQ ID NO: 4 (1-121) | QVQLQQPGA.ELVKPGASVKMSCKAS | GYTF...TSYN | MHWVKQTPGRGLEWIGA | IYPG...NGDT |
| alemtuzumab² SEQ ID NO: 5 (1-121) | QVQLQESGP.GLVRPSQTLSLTCTVS | GFTF...TDF | MNWVRQPPGRGLEWIGF | ISDKA.GYTT |
| bevacizumab SEQ ID NO: 6 (1-123) | EVQLVESGG.GLVQPGGSLRLSCAAS | GYTF...TNY | MNWVRQAPGKGLEWVG | IN.Y...TGEP |
| trastuzumab³ SEQ ID NO: 7 (1-119) | EVQLVESGG.GLVQPGGSLRLSCAAS | GFNI...KDTY | IHWVRQAPGKGLEWVA | IYPT...NGYT |
| pertuzumab SEQ ID NO: 8 (1-119) | EVQLVESGG.GLVQPGGSLRLSCAAS | GFTF...T.Y.T | MDWVRQAPGKGLEWVAD | V.P...SGGS |
| panitumumab SEQ ID NO: 9 (1-96) | .........VS | GGSVS...SGDYY. | WTWIRQSPGKGLEWIGH | IYYS...GNT |

| VH domain | FR3-IMGT | CDR3-IMGT | FR4IMGT |
|---|---|---|---|
| certuximab SEQ ID NO: 3 (1-119) | DYNTPFT.SRLSINKDNSKSQVFFKMNSLQSNDTAIYYC | ARALTY...D.FAY | WGQGTLVTVSA |
| rituximab¹ SEQ ID NO: 4 (1-121) | SYNQKFX.GKATLTADKSSSTAYMQLSSLTSEDSAVYYC | ARSTYYG...GDWYFNV | WGAGTTVTVSA |
| alemtuzumab² SEQ ID NO: 5 (1-121) | EYNPSVK.GRVTMLVDTSKNQFSLRLSSVTAADTAVYYC | AR....AAPFDY | WGQGSLVTVSS |
| bevacizumab SEQ ID NO: 6 (1-123) | TYAADFK.RRFTFSLDTSKSTAYLQMNSLRAEDTAVYYC | AX...HWYFDV | WGQGTLVTVSS |

-continued

| | | | | |
|---|---|---|---|---|
| trastuzumab[3] SEQ ID NO: 7 (1-119) | RYADSVK.GRFTISADTSKNTAYLQMNSLRAEDTAV YYC | | SRWGGD...FYAMDY | WCQGTLVTVSS |
| pertuzumab SEQ ID NO: 8 (1-119) | IYNQRFK.GRFTLSVDRSKNTLYLQMNSLRAEDTAV YYC | | ARNLG...SPFFDY | WGQGTLVTVSS |
| panitumumab SEQ ID NO: 9 (1-96) | NYNPSLK.SRLTISIDTSKTQFSLKLSSVTAADTAIYY C | | VRDRVT...GAFDI | WGQGTMVTVSS |

| V-kappa domain | FR1-IMGT | CDR1-IMGT | FR2-IMGT | CDR2-IMGT |
|---|---|---|---|---|
| certuximab SEQ ID NO: 3 (120-226) | DILLTQSPVILSVSPGERVSFSCRA S | QSI...GTN | IHWYQQRTNGSPRLLI K | YA...S |
| rituximab SEQ ID NO: 4 (122-226) | QIVLSQSPAILSASPGEKVTMTCR AS | SSV...SY | IHWFQQKPGSSPKPWI Y | AT...S |
| alemtuzumab SEQ ID NO: 5 (122-228) | DIQMTQSPSSLSASVGDRVTITCK AS | QNI...DKY | LNWYQQKPGKAPKLLI Y | NT...N |
| bevacizumab SEQ ID NO: 6 (124-230) | DIQMTQSPSSLSASVGDRVTITCS AS | QDI...SNY | LNWYQQKPGKAPKVLI Y | FT...S |
| trastuzumab SEQ ID NO: 7 (120-225) | DIQMTQSPSSLSASVGDRVTITCR AS | QDV...NTA | VAWYQQKPGKAPKLLI Y | SA...S |
| pertuzumab SEQ ID NO: 8 (120-226) | DIQMTQSPSSLSASVGDRVTITCK AS | QDV...SIG | VAWYQQKPGKAPKLLI Y | SA...S |
| panitumumab SEQ ID NO: 9 (97-184) | ........TITCQAS | QDI...SNY | LNWYQQKPGKAPKLLI Y | DA...S |

| V-kappa domain | FR3-IMGT | CDR3-IMGT | FR4IMGT |
|---|---|---|---|
| certuximab SEQ ID NO: 3 (120-226) | ESISGIP.SRFSGSG..SGTDFTLSINSVESEDIADYYC | QQNNN...WPTT | FGAGTKLELK. |
| rituximab SEQ ID NO: 4 (122-226) | NLASGVP.VRFSGSG..SGTSYSLTISRVEAEDAATY YC | QQWTS...NPPT | FGGGTKLEIK |
| alemtuzumab SEQ ID NO: 5 (122-228) | NLQTGVP.SRFSGSG..SGTDFTFTISSLQPEDIATYY C | LQHIS...RT | FGQGTKVIEK. |
| bevacizumab SEQ ID NO: 6 (124-230) | SLHSGVP.SRFSGSG..SGTDFTLTISSLQPEDFATYY C | QQYST...VPWT | FGQGTKVEIK. |
| trastuzumab SEQ ID NO: 7 (120-225) | FLYSGVP.SRFSGSR..SGTDFTLTISSLQPEDFATYY C | QQHYT...PPT | FGQGTKVEIK. |
| pertuzumab SEQ ID NO: 8 (120-226) | YRYTGVP.SRFSGSG..SGTDFTLTISSLQPEDFATY YC | QQYI...YPYT | FGQGTKVEIK. |
| panitumumab SEQ ID NO: 9 (97-184) | NLETGVP.SRFSGSG..SGTDFTFTISSLQPEDIATYF C | QHFDH...LPLA | FGGGTKVEIK. |

[1] In WO9411026 PATENT, P15 > A15.
[2] In U.S. Pat. No. 5,846,534, F28 > S28 and T35 > 835.
[3] In U.S. Pat. No. 5,821,337, Y117 > V117.
[4] In U.S. Pat. No. 5,821,337, Y68 > E68.

The CDRs of ipilimumab are given in the US patent 2009/0074787 A1.

Shown below is an alignment of the VH and V-kappa domains of bevacizumab (SEQ ID NO:10) VH domain at amino acids 1 to 123 and V-kappa domain at amino acids 124-230 and ranibizumab (SEQ ID NO:11) VH domain at amino acids 1 to 122 and V-kappa domain at amino acids 123-229.

body comprising a heavy chain and a light chain, the heavy chain comprising a sequence that is at least 90% identical to SEQ ID NO:1 and the light chain comprising a sequence that is at least 90% identical to SEQ ID NO:2 and one or more agents, e.g., imaging or therapeutic agents. Optionally, the agents are conjugated to the antibody. Optionally, the therapeutic agent is a chemotherapeutic agent. Optionally, the conjugate comprises a recombinant antigen binding protein

| VH domain | FR1-IMGT | CDR1-IMGT | FR2-IMGT | CDR2-IMGT |
|---|---|---|---|---|
| bevacizumab SEQ ID NO: 10 (1-123) | EVQLVESGG.GLVQPGGSLRLSCA AS | GYTF...TNYG | MNWVRQAPGKGLEW VGW | INTY...TGEP |
| ranibizumab SEQ ID NO: 11 (1-122) | EVQLVESGG.GLVQPGGSLRLSCA AS | GYDR...THYC | MNWVRQAPGKGLEW VGW | INTY...TGEP |

| VH domain | FR3-IMGT | CDR3-IMGT | FR4IMGT |
|---|---|---|---|
| bevacizumab SEQ ID NO: 10 (1-123) | TYAADFK.RRFTFSLDTSKSTAYLQMNSLRAEDTAVY YC | AKYPHYYGSSHWYFD V | WGQGTLVTVSS |
| ranibizumab SEQ ID NO: 11 (1-122) | TYAADFK.RRFTFSLDTSKSTAYLQMNSLRAEDTAVY YC | AKYPYYYGTSHVVYFD V | WGQGTLVTVSS |

| V-KAPPA domain | FR1-IMGT | CDR1-IMGT | FR2-IMGT | CDR2-IMGT |
|---|---|---|---|---|
| bevacizumab SEQ ID NO: 10 (124-230) | DIQMTQSPSSLSASVGDRVTITCS AS | QDI...SNY | LNWYQQKPGKAPKVL Y | IFT...S |
| ranibizumab SEQ ID NO: 11 (123-229) | DIQLTQSPSSLSASVGDRVTITCSA S | QDI...SNY | LNWYQQKPGKAPKVL Y | IFT...S |

| V-KAPPA domain | FR3-IMGT | CDR3-IMGT | FR4IMGT |
|---|---|---|---|
| bevacizumab SEQ ID NO: 10 (124-230) | SLHSGVP.SRFSGSG...SGTDFILTISSLQPEDFATYYC | QQYST...VPWT | FGQGTKVEIK. |
| ranibizumab SEQ ID NO: 11 (123-229) | SLHSGVP.SRFSGSG...SGTDFILTISSLQPEDFATYYC | QQYST...VPWT | FGQGTKVEIK. |

In another aspect, the present invention features the antibodies, or fragments thereof, disclosed herein conjugated to a therapeutic moiety, such as a cytotoxin, a drug (e.g., an immunosuppressant) or a radiotoxin. Such conjugates are referred to herein as "immunoconjugates".

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Since pritumumab can cross the blood brain barrier it can be used as a delivery vehicle for delivering other agents, e.g., imaging or therapeutic agents to the brain or other tumor tissues. Thus, provided are composition comprising an antibody as described herein conjugated to one or more agents. Optionally, the composition is formulated for delivery to the brain. Optionally, the composition is capable of crossing the blood brain barrier. Optionally, the heavy chain of the antibody comprises SEQ ID NO:1 and the light chain comprises SEQ ID NO:2. Optionally, the antibody is pritumumab.

Techniques for conjugating such therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Also provided are methods of delivering an agent to the brain of a subject. The method includes administering to the subject a composition comprising an antibody comprising a heavy chain and a light chain, the heavy chain comprising a sequence that is at least 90% identical to SEQ ID NO:1 and the light chain comprising a sequence that is at least 90% identical to SEQ ID NO:2 and one or more agents, e.g., imaging or therapeutic agents. Optionally, the therapeutic agent is a chemotherapeutic agent. Optionally, the heavy chain comprises SEQ ID NO:1 and the light chain comprises SEQ ID NO:2. Optionally, the antibody is pritumumab. Optionally, the antibody specifically binds tumor cells but not normal cells.

Suitable therapeutic agents for use in the provided compositions and methods, e.g., for conjugation to the provided antibodies include, but are not limited to, therapeutic agent is selected from the group consisting of analgesics, anesthetics, analeptics, corticosteroids, anticholinergic agents, anticholinesterases, anticonvulsants, antineoplastic agents, allosteric inhibitors, anabolic steroids, antirheumatic agents, psychotherapeutic agents, neural blocking agents, anti-inflammatory agents, antihelmintics, antibiotics, anticoagulants, antifungals, antihistamines, antimuscarinic agents, antimycobacterial agents, antiprotozoal agents, antiviral agents, dopaminergics, hematological agents, immunological agents, muscarinics, protease inhibitors, vitamins, growth factors, and hormones. The choice of agent and dosage can be determined readily by one of skill in the art based on the given disease being treated.

As described herein, the antibodies can be linked or conjugated to an imaging agent. Imaging agents and their use are known. Optionally, the imaging agent is a "detectable moiety," which is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, Bioconjugate Techniques 1996, Academic Press, Inc., San Diego. The detectable moiety can be selected from the group consisting of gamma-emitters, beta-emitters, and alpha-emitters, gamma-emitters, positron-emitters, X-ray-emitters and fluorescence-emitters. Suitable fluorescent compounds include fluorescein sodium, fluorescein isothiocyanate, phycoerythrin, and Texas Red sulfonyl chloride, Allophycocyanin (APC), Cy5-PE, CY7-APC, and Cascade yellow.

Optionally the detectable moiety can be visualized using histochemical techniques, ELISA-like assays, confocal microscopy, fluorescent detection, cell sorting methods, nuclear magnetic resonance, radioimmunoscintigraphy, X-radiography, positron emission tomography, computerized axial tomography, magnetic resonance imaging, and ultrasonography.

Antibody Assays

A number of screening assays are known in the art for assaying antibodies of interest to confirm their specificity and affinity and to determine whether those antibodies cross-react with other proteins.

The terms "specific binding" or "specifically binding" refer to the interaction between the antigen and their corresponding antibodies. The interaction is dependent upon the presence of a particular structure of the protein recognized by the binding molecule (i.e., the antigen or epitope). In order for binding to be specific, it should involve antibody binding of the epitope(s) of interest and not background antigens.

Once antibodies are produced, they are assayed to confirm that they are specific for the antigen of interest and to determine whether they exhibit any cross reactivity with other antigens. One method of conducting such assays is a sera screen assay as described in U.S. App. Pub. No. 2004/0126829, the contents of which are hereby expressly incorporated herein by reference. However, other methods of assaying for quality control are within the skill of a person of ordinary skill in the art and therefore are also within the scope of the present disclosure.

Antibodies, or antigen-binding fragments, variants or derivatives thereof of the present disclosure can also be described or specified in terms of their binding affinity to an antigen. The affinity of an antibody for an antigen can be determined experimentally using any suitable method. (See, e.g., Berzofsky et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_a$) are preferably made with standardized solutions of antibody and antigen, and a standardized buffer.

The affinity binding constant ($K_{aff}$) can be determined using the following formula:

$$K_{aff} = \frac{(n-1)}{2(n[mAb']_t - [mAb]_t)}$$

in which:

$$n = \frac{[mAg]_t}{[mAg']_t}$$

[mAb] is the concentration of free antigen sites, and [mAg] is the concentration of free monoclonal binding sites as determined at two different antigen concentrations (i.e., $[mAg]_t$ and $[mAg]_t$) (Beatty et al., J Imm Meth, 100:173-179 (1987)).

Surface plasmon resonance (SPR) can be used for detection and measurement of antibody-antigen affinity and kinetics. (See, e.g., Hearty, S., et al., Methods Mol. Biol., 907:411-42 (2012); Malmqvist, M., Current Opinion in Immunology, 5: 282-286 (1993); Chatellier, J, et al., J. Molecular Recognition, 9: 39-51 (1996); Margulies, D. H., et al., Current Opinion in Immunology, 8: 262-270 (1996); Forbes, B. E., et al., Eur. J. Biochem., 269:961-968 (2002).)

The term "high affinity" for an antibody refers to an equilibrium association constant ($K_{aff}$) of at least about $1 \times 10^7$ liters/mole, or at least about $1 \times 10^8$ liters/mole, or at least about $1 \times 10^9$ liters/mole, or at least about $1 \times 10^{10}$ liters/mole, or at least about $1 \times 10^{11}$ liters/mole, or at least about $1 \times 10^{12}$ liters/mole, or at least about $1 \times 10^{13}$ liters/mole, or at least about $1 \times 10^{14}$ liters/mole or greater. "High affinity" binding can vary for antibody isotypes. $K_D$, the equilibrium dissociation constant, is a term that is also used to describe antibody affinity and is the inverse of $K_{aff}$.

$K_D$, the equilibrium dissociation constant, is a term that is also used to describe antibody affinity and is the inverse of $K_{aff}$. If $K_D$ is used, the term "high affinity" for an antibody refers to an equilibrium dissociation constant ($K_D$) of less than about $1 \times 10^{-7}$ mole/liters, or less than about $1 \times 10^{-8}$ mole/liters, or less than about $1 \times 10^{-9}$ mole/liters, or less than about $1 \times 10^{-10}$ mole/liters, or less than about $1 \times 10^{-11}$ mole/liters, or less than about $1 \times 10^{-12}$ mole/liters, or less than about $1 \times 10^{-13}$ mole/liters, or less than about $1 \times 10^{-14}$ mole/liters or lower.

The production of antibodies according to the present disclosure provides for antibodies with the characteristics of those produced in the course of a physiological human immune response, i.e. antibody specificities that can only be selected by the human immune system. These antibodies can be used as prophylactic or therapeutic agents upon appropriate formulation.

In relation to a particular agent, a "neutralizing antibody", "broadly neutralizing antibody", or "neutralizing monoclonal antibody", all of which are used interchangeably herein, is one that can neutralize the ability of that agent to function in a host. In some embodiments, monoclonal antibodies produced in accordance with the present disclosure have neutralizing activity, where the antibody can neutralize at a concentration of $10^{-9}$M or lower (e.g., $10^{-10}$ M, $10^{-11}$ M, $10^{-12}$M or lower).

The immunoglobulin molecules of the present invention can be of any type (e.g., IgG, IgE, IgM, IgD, IgA and IgY), class (e.g., IgG1, IgG2, IgG3, IgG4, IgA1 and IgA2), or subclass of immunoglobulin molecule. In some embodiments, the antibodies are antigen-binding antibody fragments (e.g., human) and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, can comprise the variable region(s) alone or in combination with the entirety or a portion of the following: hinge region, CH1, CH2, and CH3 domains. Also included in the present disclosure are antigen-binding fragments comprising any combination of variable region(s) with a hinge region, CH1, CH2, and CH3 domains.

Recombinant Expression

The methods of the present disclosure also provide utilizing a nucleic acid to generate a host cell that can express an antibody of interest.

In some embodiments, the nucleotide sequence encoding a desired antibody can be constructed and thereafter employed in a heterologous expression system, e.g., 293 cells or CHO cells. In some embodiments, an antibody can be recombinantly expressed by obtaining one or more nucleic acids (e.g. heavy and/or light chain genes) that encodes the antibody of interest and inserting the nucleic acid into a host cell in order to permit expression of the antibody of interest in that host.

Production of antibodies using recombinant DNA methods is described, for example, in U.S. Pat. No. 4,816,567. For recombinant production of the antibody, the nucleic acid encoding it is isolated and inserted into a replicable vector for further cloning (amplification of the DNA) or for expression. DNA encoding a monoclonal antibody is readily isolated and sequenced using conventional procedures (e.g., by using oligonucleotide probes that are capable of binding specifically to genes encoding the heavy and light chains of the antibody). Vectors that can be used generally include, but are not limited to, one or more of the following: a signal sequence, an origin of replication, one or more marker genes, an enhancer element, a promoter, and a transcription termination sequence. Examples of such expression system components are disclosed in, for example, U.S. Pat. No. 5,739,277. Suitable host cells for cloning or expressing the DNA in the vectors herein are the prokaryotic, yeast, or higher eukaryotic cells (see, e.g., U.S. Pat. No. 5,739,277).

Pharmaceutical Compositions

The presently disclosed subject matter provides pharmaceutical compositions comprising the antibodies and antigen binding proteins produced in accordance with the present disclosure. In some embodiments, a pharmaceutical composition can comprise one or more antibodies or antigen binding proteins produced in using the methods disclosed herein. In some embodiments, a panel of antibodies or antigen binding proteins produced according to the present disclosure can be included in a pharmaceutical composition. In some embodiments, the antibodies or antigen binding proteins produced according to the present disclosure can be included with one or more additional agents, for example, antiviral or anticancer drugs or analgesics.

In some embodiments a pharmaceutical composition can also contain a pharmaceutically acceptable carrier or adjuvant for administration of the antibody or antigen binding protein. In some embodiments, the carrier is pharmaceutically acceptable for use in humans. The carrier or adjuvant should not itself induce the production of antibodies harmful to the individual receiving the composition and should not be toxic. Suitable carriers can be large, slowly metabolized macromolecules such as proteins, polypeptides, liposomes, polysaccharides, polylactic acids, polyglycolic acids, polymeric amino acids, ammo acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonate and benzoates.

Pharmaceutically acceptable carriers in therapeutic compositions can additionally contain liquids such as water, saline, glycerol and ethanol. Additionally, auxiliary substances, such as wetting or emulsifying agents or pH buffering substances, can be present in such compositions. Such carriers enable the pharmaceutical compositions to be formulated as tablets, pills, dragees, capsules, liquids, gels, syrups, slurries and suspensions, for ingestion by the patient.

The compositions of the presently disclosed subject matter can further comprise a carrier to facilitate composition preparation and administration. Any suitable delivery vehicle or carrier can be used, including but not limited to a microcapsule, for example a microsphere or a nanosphere (Manome et al. (1994) Cancer Res 54:5408-5413; Saltzman & Fung (1997) Adv Drug Deliv Rev 26:209-230), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al. (1997) Cancer Res 57:1447-1451 and U.S. Pat. Nos. 4,551,482, 5,714,166, 5,510,103, 5,490,840, and 5,855,900), and a polysome (U.S. Pat. No. 5,922,545).

Antibody sequences can be coupled to active agents or carriers using methods known in the art, including but not limited to carbodiimide conjugation, esterification, sodium periodate oxidation followed by reductive alkylation, and glutaraldehyde crosslinking (Goldman et al. (1997) Cancer Res. 57:1447-1451; Cheng (1996) Hum. Gene Ther. 7:275-282; Neri et al. (1997) Nat. Biotechnol. 15:1271-1275; Nabel (1997) Vectors for Gene Therapy. In Current Protocols in Human Genetics, John Wiley & Sons, New York; Park et al. (1997) Adv. Pharmacol. 40:399-435; Pasqualini et al. (1997) Nat. Biotechnol. 15:542-546; Bauminger & Wilchek (1980) Meth. Enzymol. 70:151-159; U.S. Pat. No. 6,071,890; and European Patent No. 0 439 095).

A therapeutic composition of the present invention comprises in some embodiments a pharmaceutical composition that includes a pharmaceutically acceptable carrier. Suitable formulations include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS in the range of in some embodiments 0.1 to 10 mg/ml, in some embodiments about 2.0 mg/ml; and/or mannitol or another sugar in the range of in some embodiments 10 to 100 mg/ml, in some embodiments about 30 mg/ml; and/or phosphate-buffered saline (PBS). Any other agents conventional in the art having regard to the type of formulation in question can be used. In some embodiments, the carrier is pharmaceutically acceptable. In some embodiments the carrier is pharmaceutically acceptable for use in humans.

Pharmaceutical compositions of the present disclosure can have a pH between 5.5 and 8.5, preferably between 6 and 8, and more preferably about 7. The pH can be maintained by the use of a buffer. The composition can be sterile and/or pyrogen free. The composition can be isotonic with respect to humans. Pharmaceutical compositions of the presently disclosed subject matter can be supplied in hermetically-sealed containers.

Pharmaceutical compositions can include an effective amount of one or more antibodies as described herein. In some embodiments, a pharmaceutical composition can comprise an amount that is sufficient to treat, ameliorate, or prevent a desired disease or condition, or to exhibit a detectable therapeutic effect. Therapeutic effects also include reduction in physical symptoms. The precise effective amount for any particular subject will depend upon their size and health, the nature and extent of the condition, and therapeutics or combination of therapeutics selected for administration. The effective amount for a given situation is determined by routine experimentation as practiced by one of ordinary skill in the art.

Treatment Regimens: Pharmacokinetics

The pharmaceutical compositions of the invention can be administered in a variety of unit dosage forms depending upon the method of administration. Dosages for typical antibody pharmaceutical compositions are well known to those of skill in the art. Such dosages are typically advisory in nature and are adjusted depending on the particular therapeutic context or patient tolerance. The amount antibody adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's; Egleton, *Peptides* 18: 1431-1439, 1997; Langer, *Science* 249: 1527-1533, 1990.

For purposes of the present invention, a therapeutically effective amount of a composition comprising an antibody, contains about 0.05 to 1500 µg protein, preferably about 10 to 1000 µg protein, more preferably about 30 to 500 µg and most preferably about 40 to 300 µg, or any integer between these values. For example, antibodies of the invention can be administered to a subject at a dose of about 0.1 µg to about 200 mg, e.g., from about 0.1 µg to about 5 µg, from about 5 µg to about 10 µg, from about 10 µg to about 25 µg, from about 25 µg to about 50 µg, from about 50 µg to about 100 from about 100 µg to about 500 from about 500 µg to about 1 mg, from about 1 mg to about 2 mg, with optional boosters given at, for example, 1 week, 2 weeks, 3 weeks, 4 weeks, two months, three months, 6 months and/or a year later. It is understood that the specific dose level for any particular patient depends upon a variety of factors including the activity of the specific antibody employed, the age, body weight, general health, sex, diet, time of administration, route of administration, and rate of excretion, drug combination and the severity of the particular disease undergoing therapy.

Routes of administration include, but are not limited to, oral, topical, subcutaneous, intramuscular, intravenous, subcutaneous, intradermal, transdermal and subdermal. Depending on the route of administration, the volume per dose is preferably about 0.001 to 10 ml, more preferably about 0.01 to 5 ml, and most preferably about 0.1 to 3 ml. Compositions can be administered in a single dose treatment or in multiple dose treatments on a schedule and over a time period appropriate to the age, weight and condition of the subject, the particular antibody formulation used, and the route of administration.

Kits

The invention provides kits comprising antibodies produced in accordance with the present disclosure which can be used, for instance, for therapeutic applications described above. The article of manufacture comprises a container with a label. Suitable containers include, for example, bottles, vials, and test tubes. The containers can be formed from a variety of materials such as glass or plastic. The container holds a composition which includes an active agent that is effective for therapeutic applications, such as described above. The active agent in the composition can comprise the antibody. The label on the container indicates that the composition is used for a particular therapy or non-therapeutic application, and can also indicate directions for either in vivo or in vitro use, such as those described above.

The following examples of specific aspects for carrying out the present invention are offered for illustrative purposes only, and are not intended to limit the scope of the present invention in any way.

EXAMPLES

Example 1. Pritumumab Penetrates the Blood Brain Barrier

Figure 2:
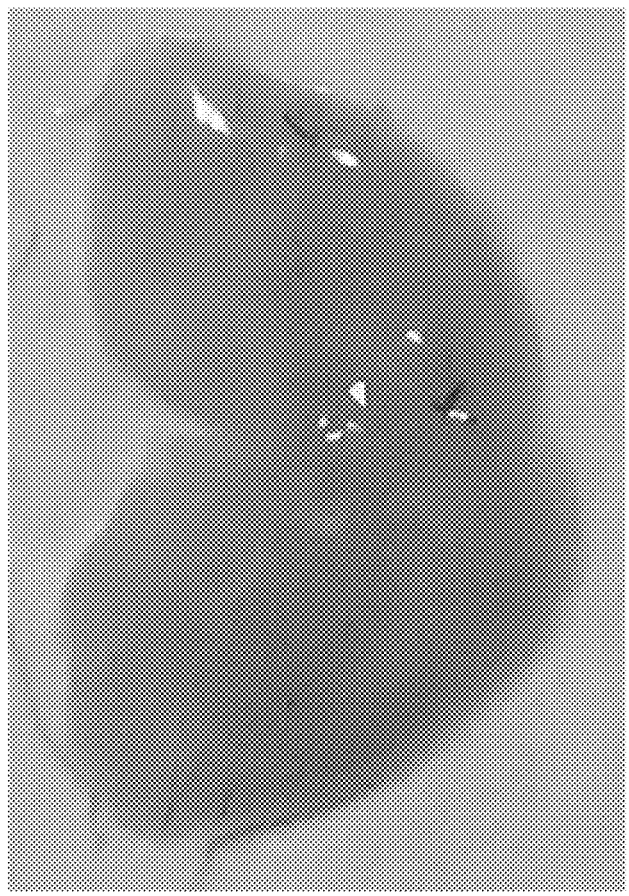
FIG. 2 is an image showing pritumumab crosses the blood brain barrier and is detected in tumor tissue in the brain.
Figure 3:
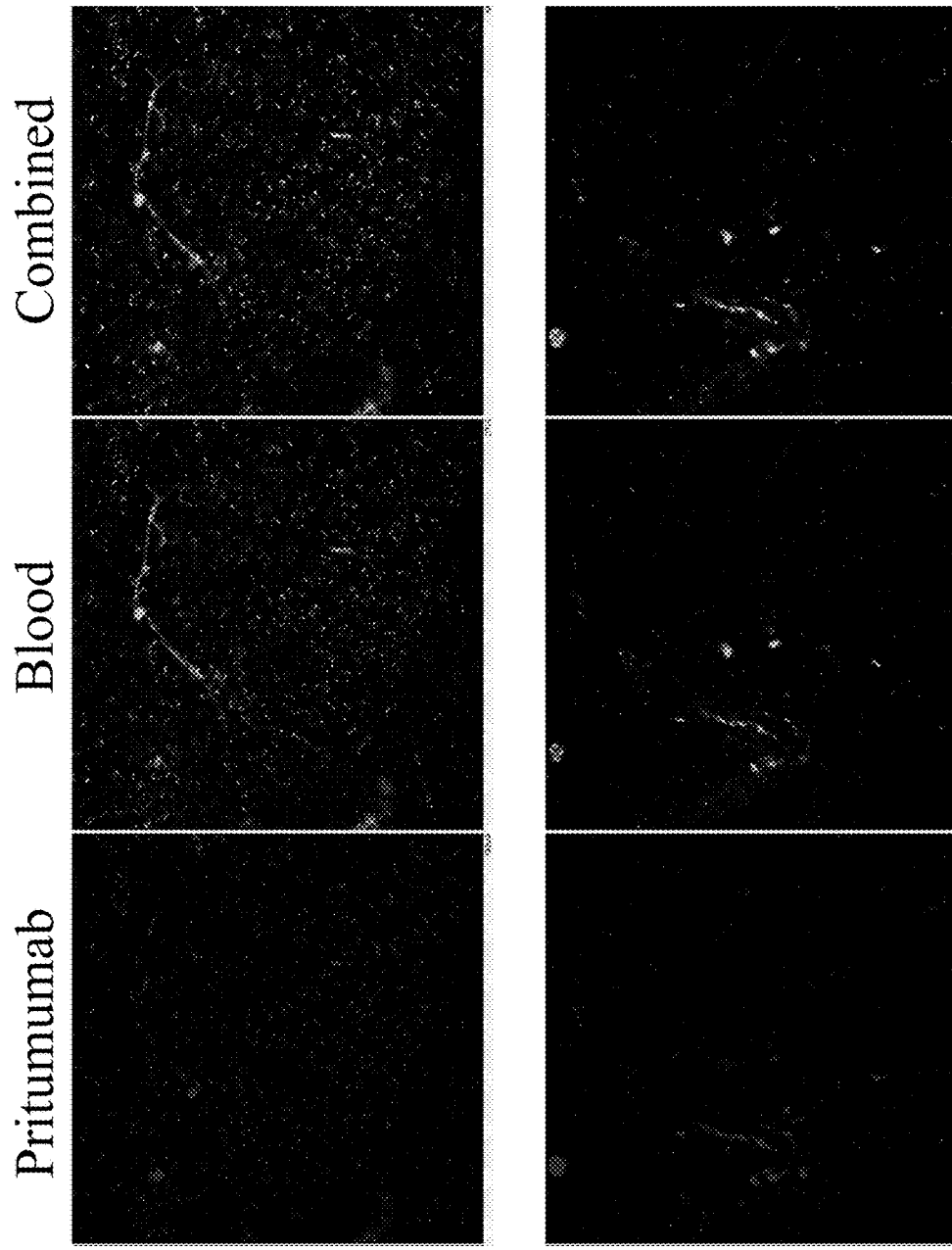
FIG. 3 is an image showing pritumumab distribution in normal brain tissue.
Figure 4:
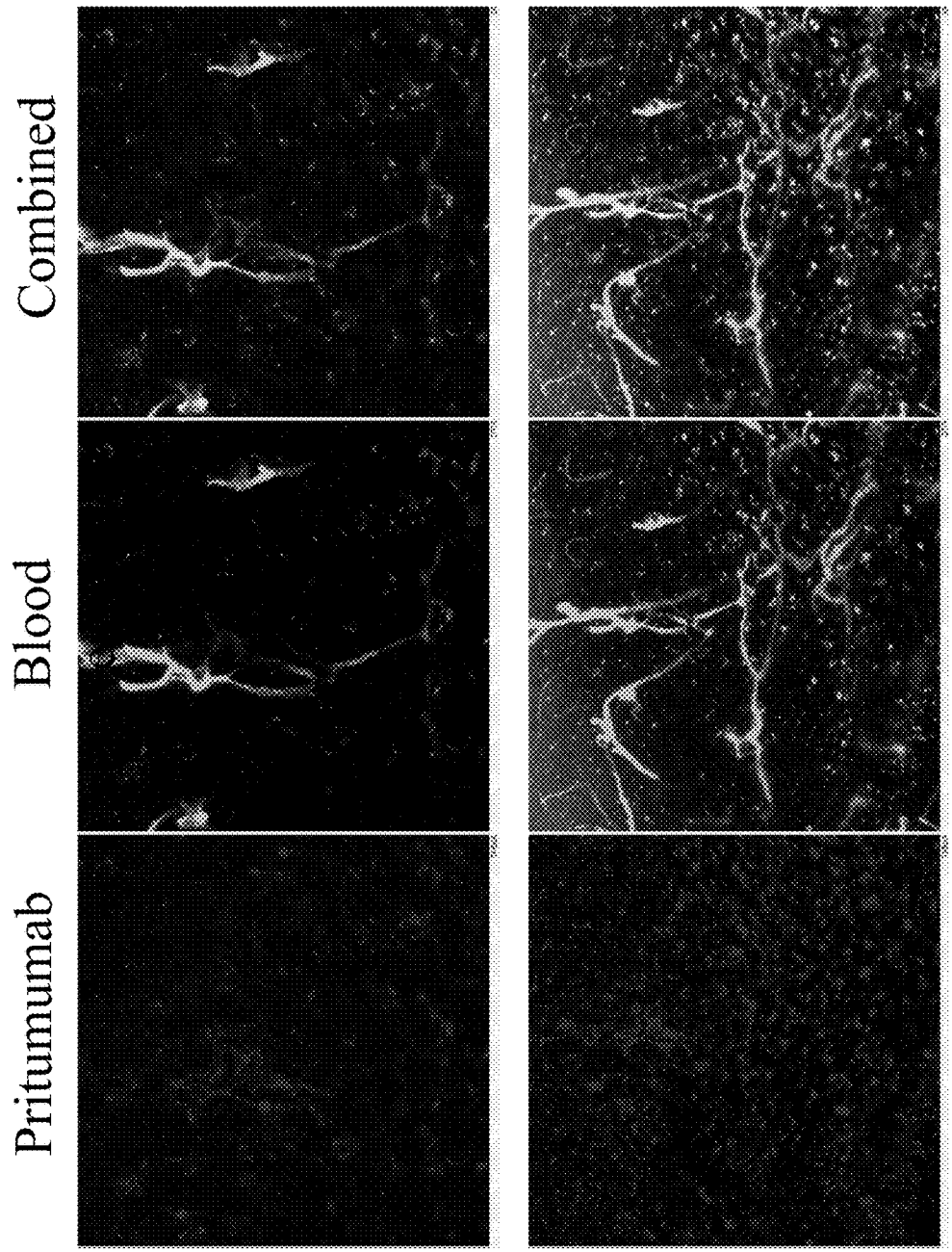
FIG. 4 is an image showing pritumumab distribution in brain tumor tissue.

To demonstrate pritumumab crosses the blood brain barrier, human primary glioblastoma stem cells (GBM8 cells;

200K cells) were injected intracranially into NSG mouse brain. After 35 days, mouse was injected intraveneously (i.v.) via tail vein with 50 μg of Pritumumab-Alexa647 antibody. After 3.5 hours 20 μg fluorescein-labeled *G. simplicifolia* lectin that binds selectively to mouse endothelial cells (GSL I-BSL I; Vector Laboratories, Inc., Burlingame, Calif.) was injected i.v. The mouse was then euthanized, brain was removed, sliced, and various areas were imaged by confocal microscopy (Nikon eclipse Ti). The results are shown in FIG. 2. Pritumumab in present in brain tumor tissue but not normal tissue. To further investigate these results, the distribution of pritumumab in the brain was studied. In Normal brain areas, the Pritumumab antibody is mostly in the normal, intact blood vessels with very little leakage around vessels at 4 hours after injection (FIG. 3). In Tumor areas, the Pritumumab antibody is mostly outside of tortuous, large, leaky tumor blood vessels within the tumors at 4 hours after injection (FIG. 4).

The distribution of pritumumab was further studied in brain and other tissues. SCID mice of either sex and typically weighing between 20-25 g were housed in microisolator cages with autoclaved bedding and autoclaved food and water. A limitation of this model is that it involves the implantation of human glioma cells into athymic nu/nu or SCID mice.

For intracranial implantation, aseptic surgical methods were followed in accordance with UCSD animal research guidelines. Target cells (both the U87 cell line and patient derived GBM8 glioma cells) were concentrated into a compact suspension (1-2 ul). Mice were anesthetized with ketamine/xylazine and the head was swabbed with Betadine. Body temperature was maintained with a circulating water pad. The tumor cell suspensions were injected stereotaxically into the right frontal cortex at 1 ul/min using a 5 ul Hamilton syringe. The syringe was left in place for 5 min before retraction to prevent reflux of the injected material.

For imaging, MRI imaging of implanted tumors (both U87 and patient derived GBM8 glioma cells) was performed every week as tumors grew. After the appropriate scans the mice were sacrificed. The MRI protocol was as follows. Mice were anesthetized with a mixture of 1.5% isofluorane and 95% oxygen throughout imaging. MRI was performed on a 4.7T horizontal bore system interfaced with a commercial scanner console (Bruker BioSpin Corporation, MA) using a homogeneous quadrature birdcage head coil. Coronal T2-weighted images (T2WI) (TR/TEeff=2,000/72 ms) were acquired with a 2D fast spin echo sequence at 1 mm slice thickness with 80 um×130 um in-plane resolution. Magnevist Gd-DTPA was injected intraeritoneally at 0.7 mmol/kg and coronal T1-weighted images (T1WI) (TR/TEeff=417/24.5 ms) were acquired once before and twice after contrast injection. Post-contrast imaging was performed at 12 min after injection.

Brain enhancement represents a measure of tumor microvascular permeability and relates to how therapeutic agents might be distributed within a tumor and whether contrast agents can highlight a small tumor. The usual normalization method was used in which a ratio of contrast enhancement is determined by comparing tumor tissue to contralateral normal brain. A ratio of enhancement comparing the tumor with cervical skeletal muscle (sternocleidomastoid) was also calculated. This was performed to provide a check for the tumor versus normal brain ratio since it is possible that inaccuracies might arise from altered permeability in the reference white matter due to tumor infiltration and edema.

The tumor to contralateral white matter ratio (TWR) and the tumor-muscle enhancement ratio (TMR) were the mean signal intensity of the enhanced tumor divided by mean signal intensity of white matter and cervical muscle, respectively, at the 12 min post-contrast T1WI. Maximum enhanced regions of interest (ROI) were selected manually on the pre- and post-contrast images. The T1 and T2 acquisitions for each animal were cross-referenced to ensure proper ROI location.

For tumor morphology, all the GBM8 tumors (n=6) has a well-demarcated margin and no central necrosis was observed. The tumors had relatively uniform hyperintensity compared to surrounding brain parenchyma on T2WI and all displayed clearly visible contrast enhancement that was uniform.

Figure 5:
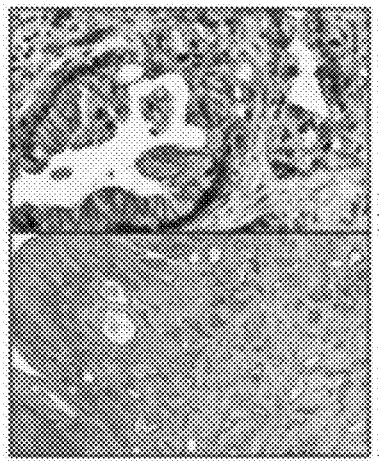
FIG. 5 are images showing pritumumab specifically binds tumor cells but not normal cells in a variety of tumor types.
Figure 5:
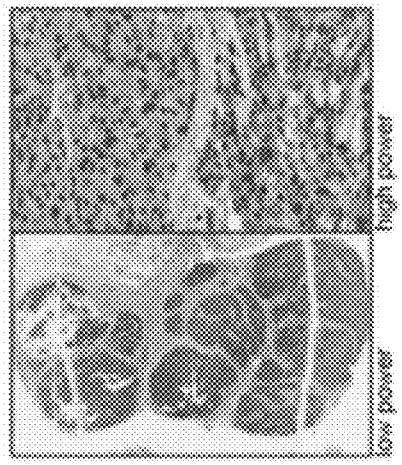
Figure 5:
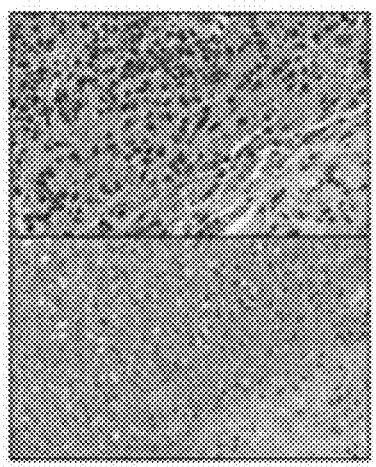
Figure 5:
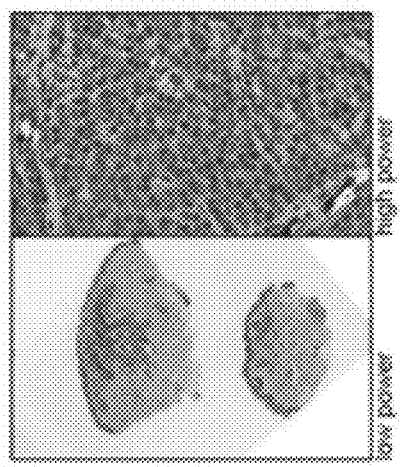
Figure 5:
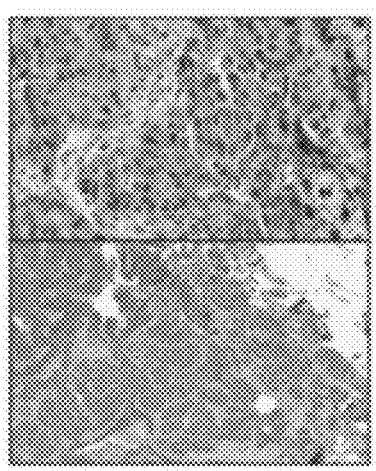
Figure 5:
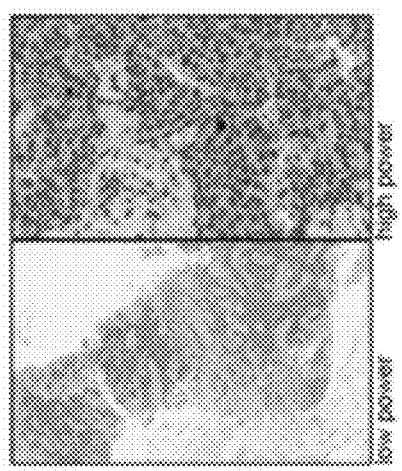

The Results are shown in FIG. 5 and Table 2. FIG. 5 are images of tissue slices showing pritumumab specifically binds to a variety of tumor cells but not normal cells. Table 2 below shows pritumumab specifically binds tumor cells but not normal cells. Pritumumab was obtained from its hybridoma or manufactured in CHO cells as described in, for example, Gupta, et al., *the Journal of Bioprocess Technology* 98:318-326 (2013) ("Gupta").

TABLE 2

Distribution in normal and tumor cells of pritumumab obtained from its hybridoma or manufactured in CHO cells.

| | Pritumumab - hybridoma | | | Pritumumab - CHO | |
| --- | --- | --- | --- | --- | --- |
| | malignant | benign | normal | malignant | normal |
| Brain | 15/27 | 2/19 | 0/8 | 10/10 | |
| Normal brain | | | | | 0/3 |
| melanoma | | | | 10/10 | |
| Colon carcinoma | | | | 2/2 | |
| Tongue | 1/1 | ND | 0/1 | | |
| Salivary gland | 0/1 | ND | ND | | |
| Thyroid | 2/2 | ND | ND | | |
| Esophagus | 1/1 | ND | 0/1 | | |
| Lung | 2/4 | ND | 0/1 | 9/9 | |
| Stomach | 2/5 | ND | 0/2 | | |
| Heart | ND | ND | 0/1 | | |
| Renal | 1/1 | ND | 0/2 | 11/11 | |
| Adrenal | 0/2 | ND | 0/1 | | |
| Spleen | 0/1 | ND | 0/3 | | |
| Liver | 0/2 | ND | 0/2 | | |
| Pancreas | 1/1 | ND | 0/1 | 9/9 | |
| Gall bladder | 2/2 | ND | 0/1 | | |
| Lymph node | 0/17 | ND | 0/3 | | |
| Breast | 5/15 | 1/5 | 0/1 | 12/12 | |
| Ovary | 6/8 | ND | 0/1 | | |
| Uterus | 2/3 | ND | 0/1 | | |
| Cervix | 7/10 | | | | 0/2 |
| Squamous epithelium | | | | | 0/2 |
| Endometrium | | | | | 0/3 |
| Blood vessels | | | | | 0/4 |
| Smooth muscle | | | | | 0/5 |
| Normal fat | | | | | 0/2 |

Example 2. Generation of Antibodies with Enhanced Delivery to the Brain Materials Cell Lines:

*E. coli* CJ236 (New England Biolabs, Beverly, Mass.); *E. coli* SS320 (Lucigen, Middleton, Wis.); *E. coli* One Shot® OmniMAX™ 2 T1R (Invitrogen, Grand Island, N.Y.); Chinese hamster ovary (CHO) cells; HEK cells.

Tumor Tissues and Tumor Cell Lines:

All tumor tissues will be discards after their clinical and diagnostic application and the cell lines will be procured from ATCC (USA). The tumor tissues will include brain, breast, cervical, colon, liver, melanoma, ovarian, and pancreatic cancers. Uterine smooth muscle will be used as normal tissue control. Inclusion of these controls will determine specificity of the recombinantly produced CDR swapped antibodies which will be equivalent to the original human-human hybridoma produced pritumumab particularly with respect to the frame-work.

Media:

One example of synthetic media is synthetic low-density lipoprotein (sLDL), as a lipid supplement in serum-free media (Hayavi and Halbert, 2005). The sLDL can be manufactured by microfluidization of the lipid dissolve in solvent with aqueous solutions, generating a non-toxic product with physico-chemical characteristic of native LDL. The inclusion of 0.1-0.5 mM iron citrate in chemically defined (animal-free) media has been shown to increase mAb expression in CHO cells by around a third, involving upregulation of genes associated with ribosome formation and protein folding (Bai et al., 2011).

Antibodies/Reagents:

Specific antibodies and other immunochemicals and routine reagents will be procured from Sigma-Aldrich and Pierce Thermo Fisher.

Pritumumab:

Pritumumab has been produced by Catalent using the patented GPEx technology.

Primer Design Using Integrated DNA Technologies Program "PRIME QUEST" for Pritumumab CDRs and Frameworks:

|  | Start | Stop | Length | Tm | GC % |
|---|---|---|---|---|---|
| HC-CDR1 primer sequence of pritumumab<br>Sequence Name: HC-CDR1 primer sequence of pritumumab<br>Amplicon Length: 242 |  |  |  |  |  |
| Forward: TCACCTTCAGCAACTATGCC (SEQ ID NO: 12) | 2 | 22 | 20 | 67 | 50 |
| Reverse: AAGGGTACCAAGTGCTTCTATATG (SEQ ID NO: 13) | 220 | 244 | 24 | 62 | 41.7 |
| HC-CDR2 primer sequence of pritumumab<br>Sequence Name: HC-CDR2 primer sequence of pritumumab<br>Amplicon Length: 281 |  |  |  |  |  |
| Forward: GAGTGGGTCTCAGCGATTAC (SEQ ID NO: 14) | 58 | 78 | 20 | 62 | 55 |
| Reverse: AGAGGTGCTCTTGGAGGA (SEQ ID NO: 15) | 321 | 339 | 18 | 62 | 55.6 |
| HC-CDR3 primer of pritumumab<br>Sequence Name: HC-CDR3 primer sequence of pritumumab<br>Amplicon Length: 213 |  |  |  |  |  |
| Forward: CTATGCCATGAGCTGGGT (SEQ ID NO: 16) | 15 | 33 | 18 | 61 | 55.6 |
| Reverse: TCTATATGGACTCTCCCACAGATA (SEQ ID NO: 17) | 204 | 228 | 24 | 62 | 41.7 |
| Framework primer sequence of HC of Pritumumab Set 1<br>Sequence Name: Framework primer sequence of HC of Pritumumab-1<br>Amplicon Length: 219 |  |  |  |  |  |
| Forward: GCCTGGTCAAAGGCTTCTAT (SEQ ID NO: 18) | 641 | 661 | 20 | 62 | 50 |
| Reverse: TCTTCTGCGTGTAGTGGTTG (SEQ ID NO: 19) | 840 | 860 | 20 | 62 | 50 |
| Framework primer sequence of HC of Pritumumab Set 2<br>Sequence Name: Framework primer sequence of HC of Pritumumab-2<br>Amplicon Length: 292 |  |  |  |  |  |
| Forward: GCTGAATGGCAAGGAGTACA (SEQ ID NO: 20) | 480 | 500 | 20 | 62 | 50 |
| Reverse: GAGCTTGCTGTAGAGGAAGAAG (SEQ ID NO: 21) | 750 | 772 | 22 | 62 | 50 |
| Framework primer sequence of HC of Pritumumab Set 3<br>Sequence Name: Framework primer sequence of HC of Pritumumab-3<br>Amplicon Length: 658 |  |  |  |  |  |
| Forward: CAAGGTGGACAAGAAAGTTGAG (SEQ ID NO: 22) | 168 | 190 | 22 | 61 | 45.5 |
| Reverse: CATCACGGAGCATGAGAAGA (SEQ ID NO: 23) | 805 | 626 | 20 | 62 | 50 |
| Framework primer sequence of HC of Pritumumab Set 4<br>Sequence Name: Framework Primer sequence of HC of Pritumumab<br>Amplicon Length: 362 |  |  |  |  |  |
| Forward: ATCACAAGCCCAGCAACA (SEQ ID NO: 24) | 149 | 167 | 31 | 62 | 50 |
| Reverse: GACCTTGCACTTGTACTCCTT (SEQ ID NO: 25) | 149 | 167 | 18 | 62 | 50 |
| Framework primer sequence of HC of Pritumumab Set 5<br>Sequence Name: Framework Primer sequence of HC of Pritumumab<br>Amplicon Length: 225 |  |  |  |  |  |
| Forward: GTGCAAGGTCTCCAACAAAG (SEQ ID NO: 26) | 500 | 521 | 21 | 63 | 47.5 |
| Reverse: GCGTGGTCTTGTAGTTGTTCTC (SEQ ID NO: 27) | 703 | 725 | 22 | 63 | 50 |

```
                                                  Start  Stop  Length  Tm   GC %

LC-CDR1 primer sequence of Pritumumab
Sequence Name: LC-CDR1 primers of Pritumumab
Amplicon Length: 261

Forward: GCATCTGTAGGAGACAGAGTCA  (SEQ ID NO: 28)    37    59    22    63    50
Reverse: GCCGAAGGTGATAGGGTAAGTA  (SEQ ID NO: 29)   276   298    22    63    50

LC-CDR2 primer sequence of Pritumumab
Sequence Name: LC-CDR2 primers of Pritumumab
Amplicon Length: 201

Forward: AGTCTCCATCCTCACTGTCT    (SEQ ID NO: 30)    17    37    20    62    50
Reverse: GAGTGAAATCTGTCCCAGATCC  (SEQ ID NO: 31)   196   218    22    62    50

LC-CDR3 primer sequence of Pritumumab
Sequence Name: LC-CDR primers of Pritumumab
Amplicon Length: 239

Forward: GAGACAGAGTCACCATCACTTG  (SEQ ID NO: 32)    47    69    22    62    50
Reverse: AGGGTAAGTACTATACTGTAGGCA (SEQ ID NO: 33)  262   286    24    62    41.7

LC Framework Primers sequence of Pritumumab Set 1
Sequence Name: LC Framework Primers for Pritumumab-1
Amplicon Length: 249

Forward: CTGCACCATCTGTCTTCATCT   (SEQ ID NO: 34)    32    53    21    62    47.6
Reverse: AGGCGTAGACTTTGTGTTTCT   (SEQ ID NO: 35)   260   281    21    62    32.9

LC Framework Primers sequence of Pritumumab Set 2
Sequence Name: LC Framework Primers for Pritumumab-2
Amplicon Length: 223

Forward: CTTCATCTTCCCGCCATCT     (SEQ ID NO: 36)    45    64    19    61    52.5
Reverse: GTGTTTCTCGTAGTCTGCTTTG  (SEQ ID NO: 37)   248   268    22    61    45.5

LC Framework Primers sequence of Pritumumab Set 3
Sequence Name: LC Framework Primers for Pritumumab-3
Amplicon Length: 209

Forward: ATCTGGAACTGCCTCTGTTG    (SEQ ID NO: 38)    78    98    20    62    50
Reverse: CTTCGCAGGCGTAGACTTT     (SEQ ID NO: 39)   268   287    19    62    52.6

LC Framework Primers sequence of Pritumumab Set 4
Sequence Name: LC Framework Primers for Pritumumab-4
Amplicon Length: 241

Forward: GTTGTGTGCCTGCTGAATAAC   (SEQ ID NO: 40)    94   115    21    62    47.6
Reverse: CCCTGTTGAAGCTCTTTGTGA   (SEQ ID NO: 41)   314   335    21    63    47.6

LC Framework Primers sequence of Pritumumab Set 5
Sequence Name: LC Framework Primers for Pritumumab
Amplicon Length: 215

Forward: AGGTGGAGATCAAACGAACTG   (SEQ ID NO: 42)     8    29    21    62    47.6
Reverse: GCTGTAGGTGCTGTCCTTG     (SEQ ID NO: 43)   204   223    19    62    57.9
```

Methods:

PCR Primers and Framework Cassette:

Extended Packaging Region.

The PCR primers will be designed to amplify a portion of the Moloney Murine Leukemia Virus extended packaging region that is found in all gene constructs used in the GPEx® process. The primers shown below amplify an 85 bp fragment of the EPR.

EPR PCR primers will include:

```
EPR1    5'-GTTATGCGCCTGCGTCTGTAC-3'    (SEQ ID NO: 44)
EPR2    5'-CCGGGTGTTCAGAACTCGTC-3'     (SEQ ID NO: 45)
```

Heavy Chain.

These PCR primers are designed to amplify a portion of the human IgG1, IgG2, IgG3 and IgG4 constant regions. The primers shown below will be amplified in a 92 bp fragment of the constant region. These primers will be:

```
Human Ab heavy chain F
5'-ACGGTGTCGTGGAACTCAG-3'              (SEQ ID NO: 46)

Human Ab heavy chain R
5'-CACGCTGCTGAGGGAGTAGAGTCC-3'         (SEQ ID NO: 47)
```

Light Chain. These PCR primers are designed to amplify a portion of the human kappa constant region. The primers shown below will be amplified in a 83 bp fragment of the constant region.

LC PCR Primers:

```
Human Ab light chain (kappa) F
5'-CAAAGTACAGTGGAAGGTGGAT-3'    (SEQ ID NO: 48)

Human Ab light chain (kappa) R
5'-GTGCTGTCCTTGCTGTCCTGCTCT-3'  (SEQ ID NO: 49)
```

Control.

These PCR primers will be designed to amplify a portion of the CHO β 1, 4-galactosyltransferase gene. The primers shown below amplify an 82 bp fragment of the CHO β 1, 4-galactosyltransferase-1 gene.

Control Single Copy Gene PCR Primers:

```
CHO Internal 1
5'-AAAGATGGGCGGTCGTTATTC-3'     (SEQ ID NO: 50)

CHO Internal 2
5'-CCTGCCGGTTGCGAAATGGGATAA-3'  (SEQ ID NO: 51)
```

DNA will be isolated from the cell lines using the DNeasy genomic DNA purification kit (Catalog #69504, Qiagen, Valencia, Calif.). PCR reactions will be set up on the SYBR® Green PCR Master Mix (Catalog #4311034, Applied Biosystem, Foster City, Calif.) under the conditions described below. The samples will be run using the following cycling program on an iQ cycler from Bio-Rad (Hercules, Calif.).

PCR Reaction Setup with Respect to PCR Components Final Concentration:
SYBR® Green PCR Master Mix 12.5 µL per reaction,
Primer final concentration: 125 nM for each primer
Separate reactions will be done for each of the different primer sets using 20 ng genomic DNA for each 25 µL reaction (Diluted in nuclease free water);
Nuclease free water will be added to bring final volume to 25 µL.
Each sample (EPR and internal control) will be run in triplicate.
The Samples Will be Run Using the Following Cycling Program on an iQ Cycler from Bio-Rad for PCR Program:
Step 1: 95° C. 9 minutes (denature and activate polymerase)
Step 2: 94° C. 15 seconds (denature)
60° C. 1 minute (combined anneal and synthesis steps) 40 cycles as in Step 2
The gene copy index will be calculated by subtracting the Ct of the transgene assay (EPR, HC or LC) from the Ct for the control assay (β 1, 4-galactosyltransferase-1).

Gene Cloning into Expression Retrovector:

Pritumumab (P-mAb) Heavy Chain grafted with CDR of interest will be cloned into Expression Retrovector. In the first PCR reaction P-mAb heavy chain variable region CDS with CPS-M's (Catalent) proprietary bovine α-lactalbumin signal peptide sequence will be amplified from the synthesized DNA fragment, plasmid GDD2120.0001, using primers SP75'(5'-TTTTAAGCTTGCCGCCACCAT-GATGTCCTTTGTCT-3' (SEQ ID NO:52)) and P-mAbHC2 (5'-GCCAGGGGGAAGACCGATGGGCCCTTGGTG-GAGGCAGAGGACACGGTCACGAG GGTG CCCTGGCCCCAATA-3' (SEQ ID NO:53)). Primer SP75' will be added to a Hind III site at the 5' end and Kozak translation initiation sequence just before the translation start codon of the signal peptide. Primer P-mAbHC2 will be amplified the variable region sequences for in-frame fusion to the P-mAb heavy chain constant region by addition of an overlap between the two sequences. In the second PCR reaction the P-mAb heavy constant region will be amplified to allow for fusion with the variable region using primers P-mAbHC1 (5'TAT-TGGGGCCAGGGCACCCTCGTGACCGTGTCCTCTG CCTCCACCAAGGGCCCATCGGTCTTCCCCCTGGC-3' (SEQ ID NO:54)) and INHC2 (5'-TTTCTCGAGATCTCAT-CATTTCCCGGGAGACAGG-GAGAGGCTCTTCTGCGTGTAG TGGT-3' (SEQ ID NO:55)) and GDD2110.0004 plasmid as a DNA template. The GDD2110.0004 plasmid will be constructed by CPS-M previously and will serve as the reaction source of the heavy chain constant region sequence. Primer P-mAbHC1 will be a reverse compliment to primer P-mAbHC2 and hence will serve the purpose of configuring the amplified constant region sequence for in-frame fusion to the variable region by addition of an overlap between the two sequences. Primer INHC2 will encode the 3' end of the heavy constant region and contributed an Xho I site for easy cloning. The amplified products from PCR reactions 1 and 2 will be used as DNA template with the outermost primers SP75' and INHC2 to join the variable and the constant regions together and to amplify full-length P-mAb heavy chain CDS. The resultant PCR product will be digested with Hind III and Xho I restriction endonucleases and ligated into the retrovector plasmid pFCSnewMCS-WPRE-SIN (new ori) (GDD1008.0146) which will also be digested with the same enzymes.

The resultant clones will be sequenced through the assembled heavy chain gene and the flanking regions and a clone will be confirmed to encode the desired full-length P-mAb heavy chain CDS.

P-mAb Light Chain Gene Cloning into Expression Retrovector:

In the first PCR reaction P-mAb light chain variable region CDS with CPS-M's proprietary bovine α-lactalbumin signal peptide sequence will be amplified from the synthesized DNA fragment, plasmid GDD2120.0001, using primers SP75' (5'-TTTTAAGCTTGCCGCCACCAT-GATGTCCTTTGTCT-3' (SEQ ID NO:56)) and PmabLC2 (5'-GCGGGAAGATGAAGACAGATGGTGCAGC-CACAGTTCGCTTGATTTCCACCTTGGT GCCTCCGCCGAAGGTGATAGG-3' (SEQ ID NO:57)). Primer SP75' will be added to a Hind III site at the 5' end and Kozak translation initiation sequence just before the translation start codon of the signal peptide. Primer PmabLC2 amplified the light chain variable region sequence for in-frame fusion to the P-mAb light chain constant region by addition of an overlap between the two sequences. In the second PCR reaction the P-mAb light chain constant region will be amplified to allow for fusion with the light chain variable region using primers PmabLC1 (5'-CCTAT-CACCTTCGGCGGAGGCACCAAGGTGGAAAT-CAAGCGAACTGTGGCTGCA CCATCTGTCTT-CATCTTCCCGC-3' (SEQ ID NO:58)) and INLC2 (5'-TTTCTCGAGATCTCACTAACACTCTCCCCTGTTGA AGCTCT-3' (SEQ ID NO:59)) and GDD2103.0003 plasmid as the DNA template. The GDD2103.0003 plasmid will be constructed by CPS-M previously and in this reaction will a source of the light chain constant region sequence. Primer PmabLC1 will be a reverse compliment to primer PmabLC2 and hence will serve the purpose of configuring the amplified constant region sequence for in-frame fusion to the variable region. Primer INLC2 encoded the 3' end of the light chain constant region and contributed an Xho I site for easy cloning.

The amplified products from PCR reactions 1 and 2 will be used as the DNA templates with the outermost primers SP75' and INLC2 to join the variable and the constant regions and to amplify full-length P-mAb light chain CDS. The resultant PCR product will be digested with Hind III and Xho I restriction endonucleases and ligated into the retrovector plasmid pFCS-newMCSWPRE-SIN (new ori) (GDD1008.0146) which would have also been digested with the same enzymes. Plasmid DNA isolated from the resultant clones will be sequenced through the assembled light chain gene and the flanking regions and a clone was confirmed to encode the desired full-length P-mAb light chain CDS.

Development of Catalent Pharma Solutions-Middleton's Expression Retrovector Construct pFCS-newMCS-WPRE-SIN (new ori) (GDD1008.0146): The latest generation GPEx® expression plasmid pFCS-newMCS-WPRE-SIN (new ori) (GDD1008.0146) will be created by adding WPRE, a post-transcriptional regulatory element whose function is described below, to pFCS-newMCS-SIN (new ori) (GDD1008.0136), which is also described below. Briefly, pCNS-newMCS-WPRE (new ori), (GDD1008.0068), also described below, was digested with ClaI, and the fragment containing WPRE will be isolated and purified. The WPRE fragment will be ligated into the major vector fragment purified from the digestion of pFCS-newMCS-SIN (new ori) (GDD1008.0136) with ClaI. The recombinant molecules will be screened using the restriction endonucleases HindIII and NaeI to confirm the correct orientation of the WPRE element. The sequence of the resultant vector across the ClaI insertion sites will be confirmed.

The GPEx® expression plasmid pFCS-newMCS-SIN (new ori) (GDD1008.0136) is a self-inactivating (SIN) vector featuring a full-length human cytomegalovirus (CMV) immediate early enhancer/promoter in the 5' LTR. The full-length human CMV promoter and the mutated (SIN) version of 3' LTR will improve expression by increasing viral titers and reducing 5' LTR promoter interference. This vector is a legacy of the previous highly successful expression vector pCS-newMCS-WPRE (new ori) (GDD1008.0074). Plasmid pFCS-newMCS-SIN (new ori) (GDD1008.0136) will be constructed by removal of an EcoRI/HindIII fragment encompassing a portion of the 3' part of the Extended Packaging Region (EPR) and Neo gene (neomycin phosphotransferase, selectable marker) from plasmid pFCNS-newMCS-SIN (new ori) (GDD1008.0140) and complementing the EPR with the small EcoRI/HindIII fragment of pCSnewMCS-WPRE (new ori) (GDD1008.0074) comprising its missing part. Plasmid pCS-newMCS-WPRE (new ori) (GDD1008.0074) is GPEx® previous generation expression vector and history of its development is described below. Construct pFCNS-newMCS-SIN (new ori) (GDD1008.0140) will be derived by removing the ClaI restriction fragment containing WPRE sequence from plasmid pFCNS-newMCS-WPRE-SIN (new ori) GDD1008.0141. Plasmid pFCNS-newMCS-WPRE-SIN (new ori) (GDD1008.0141) will be created from vector pCNS-newMCS-WPRE (new ori), (GDD1008.0068) by cloning the full-length human CMV promoter amplified by PCR from plasmid pLNC-MCS (GDD1008.0001) into the 5' LTR region upstream of the Neomycin selectable marker gene. Finally, construct pCNS-newMCSWPRE (new ori); (GDD1008.0068) will be developed by the addition of the high-copy origin of replication from the plasmid pUC19 into plasmid pCNS-newMCS-WPRE (GDD1008.0033). The origins and evolution of plasmid pCNS-newMCS-WPRE (GDD1008.0033) are detailed below in the description of development of GPEx® previous basic expression vector pCSnewMCS-WPRE (new ori) (GDD1008.0074).

The plasmid pCS-newMCS-WPRE (new ori) (GDD1008.0074) will be originally derived from plasmid pLNCX II (GD0004). The pLNCX II plasmid will be recreated at Catalent Pharma Solutions-Middleton by removing the cc49 gene from the plasmid pLNC-cc49 (GDD1008.0049) which has been received from the laboratory of Dr. Paul Sondel at the University of Wisconsin-Madison. The pLNCX II plasmid is a slight modification of the pLNCX plasmid (Genbank ACCESSION M28247) created by A. D. Miller (removal of Eco RI site; Kashmiri et al. *Hybridoma* 14: 461-473 1995 performed in the laboratory of Dr. Jeffery Schlom at the National Institutes of Health). The pLNCX II plasmid will be modified with oligonucleotides to create a multiple cloning site following the hCMV promoter (plasmid pLNC-MCS GDD1008.0001). In order to enhance production of retrovector particles, the human CMV promoter will be used to replace the 5' LTR U5 region of pLNC-MCS to create plasmid pCNC-MCS (GDD1008.0085). When used in this way, the human CMV promoter on the 5' end of the LTR does not get incorporated into retrovector particles or inserted into production cell lines.

A segment from the Pol gene of the woodchuck Hepatitis B virus will be obtained from Dr. Tom Hope then at the Salk Institute (plasmid pBluescript II SK+WPRE-B11). This fragment (WPRE—Woodchuck Post-transcriptional Regulatory Element) enhances export of mRNA lacking introns from the nucleus to the cytoplasm as well as enhances expression of genes that include this sequence in their mRNA. The plasmid pBluescript II SK+WPRE-B11 sequence will be mutated by its developers to eliminate promoter function and the initiation codon for a fragment of the putative oncogene encoding protein pX. The WPRE fragment will be inserted 3' from the multiple cloning site to create plasmid pLNC-MCS-WPRE (GDD1008.0005). Later, the WPRE fragment was transferred from pLNC-MCS-WPRE into pCNC-MCS to create pCNCMCS-WPRE (GDD1008.0030).

The simian cytomegalovirus (sCMV) promoter will be procured from Dr. Tom Hope at the University of Illinois as part of the plasmid IEX, an expression plasmid for the HTLV Tax gene. Research into the literature and intellectual property background on the simian CMV promoter denotes that it is similar to the hCMV promoter in having high constitutive activity, but will be available in the public domain. The sCMV promoter fragment will be PCR amplified from the IEX plasmid and used to replace the hCMV promoter in pLNC-MCS, creating plasmid pSCMV-MCS (GDD1008.0018). The sCMV promoter fragment will be later modified by PCR to remove a Sal I site in the 5' end and cloned into pCNC-MCS-WPRE in place of the hCMV promoter to create plasmid pCNS-MCS-WPRE (GDD1008.0031).

A second set of oligonucleotides will be used to add additional restriction enzyme sites to the multiple cloning site to create plasmid pCNSnewMCS-WPRE (GDD1008.0033). To reduce the burden of excess production of neomycin phosphotransferase protein from retrovector inserts in production cell lines, the NEO gene will be removed from pCNS-newMCS-WPRE to create pCS-newMCS-WPRE (GDD1008.0054). To improve yield from plasmid preps, the *E. coli* origin of replication in pCS-newMCSWPRE will be replaced with the origin of replication from the plasmid pUC19. This will create a plasmid pCS-newMCS-WPRE (new ori), GDD1008.0074.

Cos-7 Expression:

COS7 cells were obtained from the Health Science Research Resources Bank (Osaka) is the haploid strain of *Saccharomyces*. This unit describes the use of COS cells to efficiently produce a desired protein in a short period of time. These cells express high levels of the SV40 large tumor (T) antigen, which is necessary to initiate viral DNA replication at the SV40 origin. Three factors contribute to make COS cell expression systems appropriate for the high-level, short-term expression of proteins: (1) the high copy number achieved by SV40 origin-containing plasmids in COS cells 48 hr post-transfection, (2) the availability of good COS cell expression/shuttle vectors, and (3) the availability of simple methods for the efficient transfection of COS cells. Each COS cell transfected with DNA encoding a cell-surface antigen (in the appropriate vector) or cytoplasmic protein will express several thousand to several hundred thousand copies of the protein 72 hr post-transfection. If the transfected DNA encodes a secreted protein, up to 10 μg of protein can be recovered from the supernatant of the transfected COS cells 1 week post-transfection. COS cell transient expression systems have also been used to screen cDNA libraries, to isolate cDNAs encoding cell-surface proteins, secreted proteins, and DNA binding proteins, and to test protein expression vectors rapidly prior to the preparation of stable cell lines.

ELISA:

A sandwich ELISA was developed using pritumumab antibody as the capture reagent. Biotin-labeled recombinant antibody will be used as the detection antibody. This homologous antibody format would be possible assuming that the target antigen would have multiple epitopes. Microtiter plates (96-well Nunc Maxisorp) will be coated with purified unlabeled pritumumab antibody at 10 μg/ml concentration in 0.5M sodium carbonate pH 9.5 overnight at 25° C. Plates will then be blocked with 1% skim milk made in Tris-Buffered Saline (TBS) containing 5 mM EDTA and 1% sucrose for 4 hours at 25° C. Plates prepared in this manner could be stored dried and sealed for at least 12 months. All dilutions will be made in ImmunoBooster buffers (Bioworld Consulting Laboratories, LLC) supplemented with 20 mM EDTA. Wash buffer will be TBS containing 0.05% Tween-20 nonionic detergent. A detergent extract of cultured human tumor cells will be used as a source of antigen to derive a standard curve. Units will be in cells/well. Extracts derived from human brain tumor cells will be generated in a similar manner. As indicated above, all tumor cell lines will be purchased from American Type Culture Collection (Manassas, Va.) and grown in RPMI medium containing 10% FBS (heat-inactivated) with 8 mM glutamine. To measure direct binding of the antibody to the target antigen, cells will be grown in serum-free medium for 5 days and the conditioned medium will be filtered and stored in one large lot at 4° C. The sandwich ELISAs will be performed by diluting the cell extract standard on each plate. All incubations were performed at 25° C. and all volumes will be 100 ul per well. The plates were incubated for 15 minutes and washed three times with wash buffer. The biotin-labeled pritumumab antibody will then be added to the wells at 1 μg/ml, incubated for 15 minutes, and plates will be washed three times. Peroxidase-conjugated streptavidin (1:5,000 dilution) will be added to the plates for 15 minutes, and plates will be washed three times with wash buffer and two times with TBS. The signal will be developed by the addition of TMB substrate (BioFX Laboratories Inc.) to the plates, incubation for 15 minutes, then the color reaction will be stopped with the addition of 0.5M sulfuric acid. The data was acquired by measuring absorbance at 450 nm, and analyzed using GraphPad Prism or Microsoft Excel software programs.

Immunohistochemistry (IHC):

For IHC analyses, the antibody will be purified, and will be covalently conjugated to HRP (courtesy of American Qualex) and used to analyze various tissue sections such as brain, breast, cervical, colon, liver, melanoma, and pancreatic tissue sections. Tumor tissues left after needed diagnostic and clinical evaluation of the donor will be processed or left over paraffin blocks will be used to determine reactivity in IHC of pritumumab or its hybrid CDR version. For this purpose, 5um sections will be cut from the paraffin blocks, placed on slides and dried and de-paraffinized overnight at 60° C. The slides will be heat treated for epitope retrieval using the Dako Target Retrieval Solution at pH 9 (Dako cat #52367) in conjunction with pressure cooker for 30 minutes. The slides will then be stained on Dako Autostainer by using 3% hydrogen peroxide for 5 minutes, primary antibody (HRP-pritumumab or control) at 1:25 dilution for 1 hour, polymer-based Power Vision Plus detection solution (Leica cat #PV6104) for 30 minute, and DAB for 10 minutes. The stained slides will be counterstained in hematoxylin for 1 minute, dehydrated, and cover-slip applied for pathological examination.

IEF (Isoelectric Focusing):

IEF will be performed using IsoGel Agarose of Lonza according their protocol using the pH range from 3.5 to 9.5. The IEF plates will be stained first with Coomassie Blue and then after de-staining with Silver stain.

Immunofluorescence Assay (FACS) Analysis with Soluble Antibodies:

Freshly cultured tumor cells from established cell lines (melanoma, lung, breast) will be used for FACS analysis as described elsewhere. Cells from log-phase growing cultures with greater than 95% viability will be gently scraped off, after incubation with EDTA 0.02% (Sigma), and 3×10⁵ cells per test tube will be used. Soluble pritumumab or test antibody of the selected GPEx clone will be prepared by methods described above. Tumor cells will be incubated with the antibody (diluted 1/1 in FCS RPMI 1640) at 37° C. for 1 h in pretreated (1% BSA) plastic tubes. After three washes with FCS RPMI 1640, cells will be incubated with biotin labelled anti-human IgG antibody (1:50)(Vector Lab) for 1 h at 4° C. After three wash steps (1% BSA PBS and PBS), Phycoerithrin Streptavidin (1:20) will be added for 20 minutes at 20° C. In repeat experiments FITC labeled anti human IgG (Fab')2(1:25) (Sigma-Aldrich) will be used. Immunofluorescence labelled cells will be finally fixed in 1% Formalin-PBS. Ten thousand cells will be counted in a FACS Calibur (BD Biosciences) and analyzed by Cell Quest.

Identification of CDRs and CDR Removal/Insertion—Polymerase Chain Reaction (PCR):

PCR:

Two novel approaches of recombinant PCR technology were employed to graft the CDRs from murine monoclonal antibodies (mAb) onto human antibody frameworks (Daugherty B L, DeMartino J A, Law M F, Kawka D W, Singer I I, Mark G E (1991) Polymerase chain reaction facilitates the cloning, CDR grafting, and rapid expression of a murine monoclonal antibody directed against the CD18 component of leukocyte integrins. Nucleic Acids Research, 19:2471-2476). One approach relied on the availability of cloned human variable region templates, whereas the other strategy is dependent only on human variable region protein sequence data. The transient expression of recombinant humanized antibody is generally driven by the adenovirus major late promoter and can be detected within 48 hrs post-transfection into non-lymphoid mammalian cells. Application of these approaches enables the expression of a recombinant humanized antibody just within 6 weeks after initiating the cDNA cloning of the murine mAb.

Identification of CDRs and CDR Removal/Insertion:

CDRs of interest will be identified, removed and inserted from hybridoma cells as detailed by Fields et al (Fields C, O'Connell D, Xiao S, Lee G U, Billiald P, Muzard J: (2013) Creation of recombinant antigen-binding molecules derived from hybridomas secreting specific antibodies. Nature Protocols 8:1125-1148). This protocol describes the design and development of recombinant monovalent antigen-binding molecules derived from monoclonal antibodies through rapid identification and cloning of the functional variable heavy (VH) and variable light (VL) genes and the design and cloning of a synthetic DNA sequence optimized for expression in recombinant bacteria. Typically, monoclonal antibodies are obtained from mouse hybridomas, which most often result from the fusion of B lymphocytes from immunized mice with murine myeloma cells. The protocol described here has previously been exploited for the successful development of multiple antibody-based molecules targeting a wide range of biomolecular targets. The protocol is accessible for research groups who may not be specialized in this area, and should permit the straightforward reverse engineering of functional, recombinant antigen-binding molecules from hybridoma cells secreting functional IgGs within 50 working days. Furthermore, convenient strategies for purification of antibody fragments are also described in this protocol.

Protein a Purification Method:

Purification of antibody molecules using protein A chromatography: Purification of antibody proteins will be essentially the same as the method used for purification of regular mAbs. The protocol to be used is outlined below:
1. Prepare protein A column as instructed (GE Healthcare).
2. Gently apply cell culture medium (diluted 1:1 with binding buffer) to the column by layering onto the top of the resin.
3. Wash column with 10 volumes of the wash/binding buffer, or until the absorbance of eluate at 280 nm approaches the background level.
4. To each collection tube add 100 ml 1 M Tris buffer (pH 8.0) so the eluate could be immediately neutralized.
5. To elute the antibody, gently add elution buffer to the top of the resin, collecting the eluate in a prepared collection tube (0.9 ml/tube).
6. Repeat until the entire volume has been collected, up to eight tubes.
7. Identify positive fractions by adding 10-20 µl of eluted fractions to 300 ml of Coomassie Plus Protein Assay Reagent (Pierce) (in a microtiter plate). Positive fractions show a blue reaction.
8. Combine positive fractions and dialyze against 1000-fold of sample volume of PBS overnight.
9. Measure OD280 of dialyzed sample.
10. Antibody protein concentration can be determined UV at 280 nm.
11. Check purity of the sample by SDS-PAGE. Single bands of about 200 kDa should be observed for antibody molecules under nonreducing condition, and two bands of 37.5 kDa (LC) and 62.5 kDa (HC) should be seen under reducing conditions.
12. Store purified protein at −20° C.

SDS Page:

For analysis of monoclonal antibodies using polyacrylamide gel electrophoresis, two hydrolytic fragments derived from the heavy chain of mouse IgG1 will be produced during incubation of the antibodies in Laemmli reducing sample buffer at 10° C. for 5 min as described previously (Davagnino J, Wong C, Shelton L, Mankarious S (1995) Acid hydrolysis of monoclonal antibodies. J Immunol Method. 185:177-180). The cleavage sites will be identified by amino terminal sequencing.

Western Blotting:

Expression levels of antibody in individual expression systems will be evaluated by Western blotting according to the procedure described previously (T. Matsuo, A. Yamamoto, T. Yamamoto, K. Otsuki, N. Yamazaki, M. Kataoka, H. Terada, Y. Shinohara, Replacement of C305 in heart/muscle-type isozyme of human carnitine palmitoyltransferase I with aspartic acid and other amino acids, Biochem. Genet. 48 (2010) 193-201). Specific antibody will be prepared as stated above.

Measurements of Protein Concentration:

The protein concentration of mitochondrial fractions was measured by use of a BCA protein assay kit with bovine serum albumin as the standard.

Antibody Binding Affinity:

Robust generation of IgG bispecific antibodies has been a long-standing challenge. Existing methods require extensive engineering of each individual antibody, discovery of common light chains, or complex and laborious biochemical processing. Here we combine computational and rational design approaches with experimental structural validation to generate antibody heavy and light chains with orthogonal Fab interfaces. Parental monoclonal antibodies incorporating these interfaces, when simultaneously co-expressed, assemble into bispecific IgG with improved heavy chain-light chain pairing. Bispecific IgGs generated with this approach exhibit pharmacokinetic and other desirable properties of native IgG, but bind target antigens monovalently. As such, these CDR grafted reagents may be useful in many biotechnological and therapeutic applications.

Affinity Measurement of the mAbs and CDR Grafted Antibodies:

Affinities of the mAbs containing heavy chain-light chain redesigns will be determined using surface plasmon resonance (Biacore 3000, GE Lifesciences). Fabs will be generated from the WT pritumumab IgG1 and CRD2 containing IgG1s. Goat anti-human IgG-Fc (Jackson Immunolabs, cat #109-005-098) will be diluted to 40 µm/ml in 10 mM acetate, pH 5, and immobilized to a CMS chip surface to −10,000 RU using standard 1-ethyl-3-(3-dimethylaminopropyl)carbodiimide (EDC)/N-hydroxysuccinimide (NHS) amine coupling protocols. Fc of human antibodies that will be procured from different sources will be captured on the sensorship surface by injection for 4 min at 5 µl/min. The flow will be increased to 30 µl/min and a secondary injection of each Fab (at 50, 35, 20, 10, 5, 2 or 1 nM) will be performed. The running buffer (and dilution buffer) will be HBS-EP 10 mM Hepes, 150 mM NaCl, 3 mM EDTA, 0.005% polysorbate 20. The chip surface will be regenerated by two injections of 0.1 M glycine, pH 2.0. The concentration series will be fitted to a 1:1 binding model to determine the binding (ka) and dissociation (kd) rate constants and the equilibrium dissociation constant (KD).

Mass Spectrometric Determination of Light Chain Specificity and CDR Grafted IgG Assembly:

Proteins will be purified on an Agilent 1100 HPLC using a protein G (PG) ID sensor cartridge (Life Technologies).

Purified samples will be analyzed on an Agilent 6210 time-of-flight liquid chromatography/mass spectrometry (LC/MS) system molecular weight analyzer. Theoretical mass-averaged molecular weights of the light chain and heavy chain components will be determined using the GPMaw program (v. 8.20). For the light chain competition experiments, the relative counts of the ionized light chains hitting the detector will be used to quantify the ratio of designed versus WT light chain bound to a designed or WT heavy chain.

Fab Protein Crystallization:

Fab proteins will be produced by proteolytic cleavage of the full-length IgGs using papain. Pritumumab Fab (with Cλ) crystal screening will be performed at 16 mg/ml protein. The crystals (thin microcrystalline plates) should appear after 4 days in 100 mM sodium acetate pH 4.6/30% PEG MME 2K/200 mM ammonium sulfate. Crystals will be cryo-protected in reservoir solution with PEG MME 2K. Concentration will be increased by 10% and supplemented with 20% glycerol. Improved order within the variable domains will be achieved by generating crystal in the same conditions, plus 10% MPD at 12.4 mg/ml protein. The pritumumab Fab containing the CDR will be crystallized using 15 mg/ml protein.

Structure Determination:

X-ray diffraction data will be collected under standard cryogenic conditions at the Advanced Photon Source (Argonne National Laboratory) using the LRL-CAT beamline and reduced to structure factor amplitudes using MOSFLM, SCALA and TRUNCATE. All structures will be solved using PHASER, refined using REFMAC, and visualized and rebuilt using XTALVIEW/XFIT. Structures of subsequent design mutants (CRD1 and an intermediate of CRD2) will be solved by Phaser using this parent structure as a search model. The parent Fab of pritumumab will be solved using the known structure of pritumumab and the variable domains of the antibody. The stereochemical quality of the atomic model will be monitored using an automated quality control procedure.

Phage Display Library:

By using optimized procedures that are based on the classical oligonucleotide-directed mutagenesis method of Kunkel et al., very large phage-displayed antibody repertoires (>$10^{10}$ members) can be constructed quite rapidly. Importantly, the method is scalable and can be used to mutate up to four independent regions concurrently with very high efficiency. First, a dut–/ung– E. coli host will be used to propagate phage encapsulating uracil-containing ssDNA (dU-ssDNA) template to which mutagenic oligonucleotides are annealed. "Stop templates" contain stop codons in the CDRs and ensure that only mutated antibodies are displayed, as the parental stop template will fail to express a full-length Fab-Pritumumab fusion protein. Residual template clones are therefore eliminated from the phage pools during selections. Diversity within a Fab library can be designed by using mutagenic oligonucleotides that contain mixed bases at particular positions to produce sets of degenerate codons. Alternatively, finer control of codon usage can be achieved by using oligonucleotides synthesized from sets of trinucleotides. By choosing particular codons for specific amino acids, we biased the CDR amino acids to those that are commonly found in natural antibodies or are particularly well suited for antigen recognition. Annealed mutagenic oligonucleotides to the ssDNA template will serve to prime synthesis of a complementary DNA strand forming a synthetic daughter strand lacking uracil. A ligase then fuses the synthesized DNA fragments to from covalently closed circular double-stranded heteroduplex DNA (CCC-dsDNA). The heteroduplex DNA will then be electroporated into a highly competent strain of dut+/ung+ E. coli, SS320, where the synthesized strand is preferentially amplified compared to the template strand.

Transformation into an E. coli host results in phagemid replication as a double-stranded plasmid. Upon coinfection with helper phage, single-stranded DNA (ssDNA) replication is initiated and phagemid ssDNA is packaged into phage particles containing phagemid-encoded protein, thereby providing physical linkage between the phenotype of the Fab and the encoding phagemid genotype. Helper phage, such as M13KO7, provides all proteins necessary for assembly of phage particles with some phagemid encoded fusion protein incorporated. These phage particles produced by infected cells make up both the genetic barcode and interaction readout of the Fab library as the host E. coli cells are never introduced to antigens during selections.

While specific aspects have been described and illustrated, such aspects should be considered illustrative only and not as limiting in accordance with the accompanying claims.

All publications and patent applications cited in this specification are herein incorporated by reference in their entirety for all purposes as if each individual publication or patent application were specifically and individually indicated to be incorporated by reference for all purposes.

Although the foregoing compositions and methods has been described in some detail by way of illustration and example for purposes of clarity of understanding, it will be readily apparent to one of ordinary skill in the art in light of the teachings herein that certain changes and modifications can be made thereto without departing from the spirit or scope of the appended claims.

What is claimed:

1. An antibody comprising a heavy chain and a light chain, wherein the heavy chain comprises a heavy chain acceptor framework of SEQ ID NO: 1; and wherein the light chain comprises a light chain acceptor framework of SEQ ID NO: 2, wherein the light chain CDR1, CDR2 and CDR3 at amino acids 28-34, 50-56, and 91-97 of SEQ ID NO:2, respectively, are replaced with the CDR1, CDR2 and CDR3 at amino acids 148-152, 170-172 and 208-216 of SEQ ID NO:4, respectively; and wherein the heavy chain CDR1, CDR2 and CDR3 at amino acids 31-35, 50-59, and 101-109 of SEQ ID NO:1, respectively, are replaced with the CDR1, CDR2 and CDR3 at amino acids 26-33, 51-58, and 97-110 of SEQ ID NO:4, respectively.

2. The antibody of claim 1, wherein the antibody is capable of crossing the blood brain barrier.

3. A composition comprising the antibody of claim 1 and a pharmaceutically acceptable carrier.

4. The composition of claim 3, wherein the composition is formulated for delivery to the brain.

5. The composition of claim 3, wherein the composition is capable of crossing the blood brain barrier.

* * * * *

SEQUENCE LISTING

<160> NUMBER OF SEQ ID NOS: 55

<210> SEQ ID NO 1
<211> LENGTH: 450
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Leu Glu Ser Gly Gly Asp Leu Val Gln Pro Gly Gly
1               5                   10                  15

```
Ser Leu Arg Leu Ser Cys Ala Ala Ser Gly Phe Thr Phe Ser Asn Tyr
         20                  25                  30
Ala Met Ser Trp Val Arg Gln Ala Pro Gly Lys Gly Leu Glu Trp Val
             35                  40                  45
Ser Ala Ile Thr Pro Ser Gly Gly Ser Thr Asn Tyr Ala Asp Ser Val
         50                  55                  60
Lys Gly Arg Phe Thr Ile Ser Arg Asp Asn Ser Gln Asn Thr Leu Tyr
 65                  70                  75                  80
Leu Gln Met Asn Ser Leu Arg Val Glu Asp Thr Ala Val Tyr Ile Cys
                 85                  90                  95
Gly Arg Val Pro Tyr Arg Ser Thr Trp Tyr Pro Leu Tyr Trp Gly Gln
                100                 105                 110
Gly Thr Leu Val Thr Val Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
```

```
                  435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu His Ser Lys Val Pro Thr Gln Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ser Thr Tyr Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 226
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 3

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60
```

```
Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Asp Ile Leu Leu Thr Gln Ser Pro Val
            115                 120                 125

Ile Leu Ser Val Ser Pro Gly Glu Arg Val Ser Phe Ser Cys Arg Ala
        130                 135                 140

Ser Gln Ser Ile Gly Thr Asn Ile His Trp Tyr Gln Gln Arg Thr Asn
145                 150                 155                 160

Gly Ser Pro Arg Leu Leu Ile Lys Tyr Ala Ser Glu Ser Ile Ser Gly
                165                 170                 175

Ile Pro Ser Arg Phe Ser Gly Ser Gly Ser Gly Thr Asp Phe Thr Leu
                180                 185                 190

Ser Ile Asn Ser Val Glu Ser Glu Asp Ile Ala Asp Tyr Tyr Cys Gln
            195                 200                 205

Gln Asn Asn Asn Trp Pro Thr Thr Phe Gly Ala Gly Thr Lys Leu Glu
210                 215                 220

Leu Lys
225

<210> SEQ ID NO 4
<211> LENGTH: 226
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 4

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
 65                 70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
                100                 105                 110

Ala Gly Thr Thr Val Thr Val Ser Ala Gln Ile Val Leu Ser Gln Ser
            115                 120                 125

Pro Ala Ile Leu Ser Ala Ser Pro Gly Glu Lys Val Thr Met Thr Cys
        130                 135                 140

Arg Ala Ser Ser Ser Val Ser Tyr Ile His Trp Phe Gln Gln Lys Pro
145                 150                 155                 160

Gly Ser Ser Pro Lys Pro Trp Ile Tyr Ala Thr Ser Asn Leu Ala Ser
                165                 170                 175

Gly Val Pro Val Arg Phe Ser Gly Ser Gly Ser Gly Thr Ser Tyr Ser
                180                 185                 190
```

```
Leu Thr Ile Ser Val Glu Ala Glu Asp Ala Ala Thr Tyr Tyr Cys Gln
            195                 200                 205

Gln Trp Thr Ser Asn Pro Pro Thr Phe Gly Gly Gly Thr Lys Leu Glu
    210                 215                 220

Ile Lys
225

<210> SEQ ID NO 5
<211> LENGTH: 228
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 5

Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Thr Phe Thr Asp Phe
            20                  25                  30

Tyr Met Asn Trp Val Arg Gln Pro Pro Gly Arg Gly Leu Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Val Thr Met Leu Val Asp Thr Ser Lys Asn Gln
65                  70                  75                  80

Phe Ser Leu Arg Leu Ser Ser Val Thr Ala Ala Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Ser Leu Val Thr Val Ser Ser Asp Ile Gln Met Thr Gln Ser
        115                 120                 125

Pro Ser Ser Leu Ser Ala Ser Val Gly Asp Arg Val Thr Ile Thr Cys
    130                 135                 140

Lys Ala Ser Gln Asn Ile Asp Lys Tyr Leu Asn Trp Tyr Gln Gln Lys
145                 150                 155                 160

Pro Gly Lys Ala Pro Lys Leu Leu Ile Tyr Asn Thr Asn Asn Leu Gln
                165                 170                 175

Thr Gly Val Pro Ser Arg Phe Ser Gly Ser Gly Ser Gly Thr Asp Phe
            180                 185                 190

Thr Phe Thr Ile Ser Ser Leu Gln Pro Glu Asp Ile Ala Thr Tyr Tyr
        195                 200                 205

Cys Leu Gln His Ile Ser Arg Pro Arg Thr Phe Gly Gln Gly Thr Lys
    210                 215                 220

Val Glu Ile Lys
225

<210> SEQ ID NO 6
<211> LENGTH: 230
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30
```

```
Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Asp Ile Gln Met Thr
            115                 120                 125

Gln Ser Pro Ser Ser Leu Ser Ala Ser Val Gly Asp Arg Val Thr Ile
        130                 135                 140

Thr Cys Ser Ala Ser Gln Asp Ile Ser Asn Tyr Leu Asn Trp Tyr Gln
145                 150                 155                 160

Gln Lys Pro Gly Lys Ala Pro Lys Val Leu Ile Tyr Phe Thr Ser Ser
                165                 170                 175

Leu His Ser Gly Val Pro Ser Arg Phe Ser Gly Ser Gly Ser Gly Thr
            180                 185                 190

Asp Phe Thr Leu Thr Ile Ser Ser Leu Gln Pro Glu Asp Phe Ala Thr
            195                 200                 205

Tyr Tyr Cys Gln Gln Tyr Ser Thr Val Pro Trp Thr Phe Gly Gln Gly
        210                 215                 220

Thr Lys Val Glu Ile Lys
225                 230

<210> SEQ ID NO 7
<211> LENGTH: 225
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Asp Ile Gln Met Thr Gln Ser Pro
            115                 120                 125

Ser Ser Leu Ser Ala Ser Val Gly Asp Arg Val Thr Ile Thr Cys Arg
        130                 135                 140

Ala Ser Gln Asp Val Asn Thr Ala Val Ala Trp Tyr Gln Gln Lys Pro
145                 150                 155                 160
```

```
Gly Lys Ala Pro Lys Leu Leu Ile Tyr Ser Ala Ser Phe Leu Tyr Gly
                165                 170                 175

Val Pro Ser Arg Phe Gly Ser Arg Gly Thr Asp Phe Thr Leu Thr
            180                 185                 190

Ile Ser Ser Leu Gln Pro Glu Asp Phe Ala Thr Tyr Tyr Cys Gln Gln
        195                 200                 205

His Tyr Thr Thr Pro Pro Thr Phe Gly Gln Gly Thr Lys Val Glu Ile
    210                 215                 220

Lys
225

<210> SEQ ID NO 8
<211> LENGTH: 226
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Asp Ile Gln Met Thr Gln Ser Pro Ser
        115                 120                 125

Ser Leu Ser Ala Ser Val Gly Asp Arg Val Thr Ile Thr Cys Lys Ala
    130                 135                 140

Ser Gln Asp Val Ser Ile Gly Val Ala Trp Tyr Gln Gln Lys Pro Gly
145                 150                 155                 160

Lys Ala Pro Lys Leu Leu Ile Tyr Ser Ala Ser Tyr Arg Tyr Thr Gly
                165                 170                 175

Val Pro Ser Arg Phe Ser Gly Ser Gly Ser Gly Thr Asp Phe Thr Leu
            180                 185                 190

Thr Ile Ser Ser Leu Gln Pro Glu Asp Phe Ala Thr Tyr Tyr Cys Gln
        195                 200                 205

Gln Tyr Tyr Ile Tyr Pro Tyr Thr Phe Gly Gln Gly Thr Lys Val Glu
    210                 215                 220

Ile Lys
225

<210> SEQ ID NO 9
<211> LENGTH: 184
<212> TYPE: PRT
<213> ORGANISM: ARTIFICIAL SEQUENCE
<220> FEATURE:
<223> OTHER INFORMATION: SYNTHETIC CONSTRUCT
```

```
<400> SEQUENCE: 9

Val Ser Gly Gly Ser Val Ser Ser Gly Asp Tyr Tyr Trp Arg Trp Ile
1               5                   10                  15

Arg Gln Ser Pro Gly Lys Gly Leu Glu Trp Ile Gly His Ile Tyr Tyr
            20                  25                  30

Ser Gly Asn Thr Asn Tyr Asn Pro Ser Lys Leu Ser Arg Leu Thr Ile
        35                  40                  45

Ser Ile Asp Thr Ser Lys Thr Gln Phe Ser Leu Lys Leu Ser Ser Val
50                  55                  60

Thr Ala Ala Asp Thr Ala Ile Tyr Tyr Cys Val Arg Asp Arg Val Tyr
65                  70                  75                  80

Gly Ala Phe Asp Ile Trp Gly Gln Gly Thr Met Val Thr Val Ser Ser
                85                  90                  95

Thr Ile Thr Asp Gln Ala Ser Gln Asp Ile Ser Asn Tyr Leu Asn Trp
            100                 105                 110

Tyr Gln Gln Lys Pro Gly Lys Ala Pro Lys Leu Leu Ile Tyr Asp Ala
        115                 120                 125

Ser Asn Leu Glu Thr Gly Val Pro Ser Arg Phe Ser Gly Ser Gly Ser
130                 135                 140

Gly Thr Asp Phe Thr Phe Thr Ile Ser Ser Leu Gln Pro Glu Asp Ile
145                 150                 155                 160

Ala Thr Tyr Phe Cys Gln His Phe Asp His Leu Pro Leu Ala Phe Gly
                165                 170                 175

Gly Gly Thr Lys Val Glu Ile Lys
            180

<210> SEQ ID NO 10
<211> LENGTH: 229
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
50                  55                  60

Lys Arg Arg Phe Thr Ser Leu Asp Thr Ser Lys Ser Thr Ala Tyr Leu
65                  70                  75                  80

Gln Met Asn Ser Leu Arg Ala Glu Asp Thr Ala Val Tyr Tyr Cys Ala
                85                  90                  95

Lys Tyr Pro His Tyr Tyr Gly Ser Ser His Trp Tyr Phe Asp Val Trp
            100                 105                 110

Gly Gln Gly Thr Leu Val Thr Val Ser Ser Asp Ile Gln Met Thr Gln
        115                 120                 125

Ser Pro Ser Ser Leu Ser Ala Ser Val Gly Asp Arg Val Thr Ile Thr
130                 135                 140

Cys Ser Ala Ser Gln Asp Ile Ser Asn Tyr Leu Asn Trp Tyr Gln Gln
145                 150                 155                 160

Lys Pro Gly Lys Ala Pro Lys Val Leu Ile Tyr Phe Thr Ser Ser Leu
```

165                 170                 175

His Ser Gly Val Pro Ser Arg Phe Ser Gly Ser Gly Ser Gly Thr Asp
            180                 185                 190

Phe Thr Leu Thr Ile Ser Ser Leu Gln Pro Glu Asp Phe Ala Thr Tyr
        195                 200                 205

Tyr Cys Gln Gln Tyr Ser Thr Val Pro Trp Thr Phe Gly Gln Gly Thr
    210                 215                 220

Lys Val Glu Ile Lys
225

<210> SEQ ID NO 11
<211> LENGTH: 229
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Ser Leu Asp Thr Ser Lys Ser Thr Ala Tyr Leu
65                  70                  75                  80

Gln Met Asn Ser Leu Arg Ala Glu Asp Thr Ala Val Tyr Tyr Cys Ala
                85                  90                  95

Lys Tyr Pro Tyr Tyr Tyr Gly Thr Ser His Trp Tyr Phe Asp Val Trp
            100                 105                 110

Gly Gln Gly Thr Leu Val Thr Val Ser Ser Asp Ile Gln Leu Thr Gln
        115                 120                 125

Ser Pro Ser Ser Leu Ser Ala Ser Val Gly Asp Arg Val Thr Ile Thr
    130                 135                 140

Cys Ser Ala Ser Gln Asp Ile Ser Asn Tyr Leu Asn Trp Tyr Gln Gln
145                 150                 155                 160

Lys Pro Gly Lys Ala Pro Lys Val Leu Ile Tyr Phe Thr Ser Ser Leu
                165                 170                 175

His Ser Gly Val Pro Ser Arg Phe Ser Gly Ser Gly Ser Gly Thr Asp
            180                 185                 190

Phe Thr Leu Thr Ile Ser Ser Leu Gln Pro Glu Asp Phe Ala Thr Tyr
        195                 200                 205

Tyr Cys Gln Gln Tyr Ser Thr Val Pro Trp Thr Phe Gly Gln Gly Thr
    210                 215                 220

Lys Val Glu Ile Lys
225

<210> SEQ ID NO 12
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 12
tcaccttcag caactatgcc                                              20

<210> SEQ ID NO 13
<211> LENGTH: 24
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 13
aagggtacca agtgcttcta tatg                                         24

<210> SEQ ID NO 14
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 14
gagtgggtct cagcgattac                                              20

<210> SEQ ID NO 15
<211> LENGTH: 18
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 15
agaggtgctc ttggagga                                                18

<210> SEQ ID NO 16
<211> LENGTH: 18
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 16
ctatgccatg agctgggt                                                18

<210> SEQ ID NO 17
<211> LENGTH: 24
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 17
tctatatgga ctctcccaca gata                                         24

<210> SEQ ID NO 18
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 18
gcctggtcaa aggcttctat                                              20

<210> SEQ ID NO 19
<211> LENGTH: 20
<212> TYPE: DNA
<213> ORGANISM: ARTIFICIAL SEQUENCE

```
<220> FEATURE:
<223> OTHER INFORMATION: SYNTHETIC CONSTRUCT

<400> SEQUENCE: 19
tcttctgcgt gtagtggttg                                               20

<210> SEQ ID NO 20
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 20
gctgaatggc aaggagtaca                                               20

<210> SEQ ID NO 21
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 21
gagcttgctg tagaggaaga ag                                            22

<210> SEQ ID NO 22
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 22
caaggtggac aagaaagttg ag                                            22

<210> SEQ ID NO 23
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 23
catcacggag catgagaaga                                               20

<210> SEQ ID NO 24
<211> LENGTH: 18
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 24
atcacaagcc cagcaaca                                                 18

<210> SEQ ID NO 25
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 25
gaccttgcac ttgtactcct t                                             21
```

```
<210> SEQ ID NO 26
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 26
gtgcaaggtc tccaacaaag                                                   20

<210> SEQ ID NO 27
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 27
gcgtggtctt gtagttgttc tc                                                22

<210> SEQ ID NO 28
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 28
gcatctgtag gagacagagt ca                                                22

<210> SEQ ID NO 29
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 29
gccgaaggtg atagggtaag ta                                                22

<210> SEQ ID NO 30
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 30
agtctccatc ctcactgtct                                                   20

<210> SEQ ID NO 31
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 31
gagtgaaatc tgtcccagat cc                                                22

<210> SEQ ID NO 32
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT
```

<400> SEQUENCE: 32
gagacagagt caccatcact tg                                            22

<210> SEQ ID NO 33
<211> LENGTH: 24
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 33
agggtaagta ctatactgta ggca                                          24

<210> SEQ ID NO 34
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 34
ctgcaccatc tgtcttcatc t                                             21

<210> SEQ ID NO 35
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 35
aggcgtagac tttgtgtttc t                                             21

<210> SEQ ID NO 36
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 36
cttcatcttc ccgccatct                                                19

<210> SEQ ID NO 37
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 37
gtgtttctcg tagtctgctt tg                                            22

<210> SEQ ID NO 38
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 38
atctggaact gcctctgttg                                               20

<210> SEQ ID NO 39

```
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 39
cttcgcaggc gtagactttt                                              19

<210> SEQ ID NO 40
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 40
gttgtgtgcc tgctgaataa c                                            21

<210> SEQ ID NO 41
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 41
ccctgttgaa gctctttgtg a                                            21

<210> SEQ ID NO 42
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 42
aggtggagat caaacgaact g                                            21

<210> SEQ ID NO 43
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 43
gctgtaggtg ctgtccttg                                               19

<210> SEQ ID NO 44
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 44
gttatgcgcc tgcgtctgta c                                            21

<210> SEQ ID NO 45
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 45
```

```
ccgggtgttc agaactcgtc                                                    20

<210> SEQ ID NO 46
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 46
acggtgtcgt ggaactcag                                                     19

<210> SEQ ID NO 47
<211> LENGTH: 24
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 47
cacgctgctg agggagtaga gtcc                                               24

<210> SEQ ID NO 48
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 48
caaagtacag tggaaggtgg at                                                 22

<210> SEQ ID NO 49
<211> LENGTH: 24
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 49
gtgctgtcct tgctgtcctg ctct                                               24

<210> SEQ ID NO 50
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 50
aaagatgggc ggtcgttatt c                                                  21

<210> SEQ ID NO 51
<211> LENGTH: 24
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 51
cctgccggtt gcgaaatggg ataa                                               24

<210> SEQ ID NO 52
<211> LENGTH: 35
<212> TYPE: DNA
```

```
<213> ORGANISM: ARTIFICIAL SEQUENCE
<220> FEATURE:
<223> OTHER INFORMATION: SYNTHETIC CONSTRUCT

<400> SEQUENCE: 52
ttttaagctt gccgccacca tgatgtcctt tgtct                       35

<210> SEQ ID NO 53
<211> LENGTH: 71
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 53
gccaggggga agaccgatgg gcccttggtg gaggcagagg acacggtcac gagggtgccc    60 tggcccaat a                                                         71

<210> SEQ ID NO 54
<211> LENGTH: 71
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 54
tattggggcc agggcaccct cgtgaccgtg tcctctgcct ccaccaaggg cccatcggtc    60
ttccccctgg c                                                        71

<210> SEQ ID NO 55
<211> LENGTH: 59
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 55
tttctcgaga tctcatcatt tcccgggaga cagggagagg ctcttctgcg tgtagtggt    59
```